United States Patent
Revel et al.

(10) Patent No.: US 9,631,175 B2
(45) Date of Patent: *Apr. 25, 2017

(54) METHODS OF GENERATING GLIAL AND NEURONAL CELLS AND USE OF SAME FOR THE TREATMENT OF MEDICAL CONDITIONS OF THE CNS

(71) Applicant: Yeda Research and Development Co. Ltd., Rechovot (IL)

(72) Inventors: Michel Revel, Rechovot (IL); Judith Chebath, Rechovot (IL); Michal Izrael, Rechovot (IL); Rosalia Kaufman, Rechovot (IL)

(73) Assignee: Yeda Research and Development Co. Ltd. at the Weizmann Institute of Science, Rechovot (IL)

( * ) Notice: Subject to any disclaimer, the term of this patent is extended or adjusted under 35 U.S.C. 154(b) by 123 days.

This patent is subject to a terminal disclaimer.

(21) Appl. No.: 14/329,510

(22) Filed: Jul. 11, 2014

(65) Prior Publication Data

US 2014/0322179 A1 Oct. 30, 2014

Related U.S. Application Data

(63) Continuation of application No. 12/310,495, filed as application No. PCT/IL2007/001026 on Aug. 15, 2007, now Pat. No. 8,809,052.

(60) Provisional application No. 60/840,426, filed on Aug. 28, 2006.

(51) Int. Cl.
| | |
|---|---|
| A01N 63/00 | (2006.01) |
| C12N 5/079 | (2010.01) |
| C12N 5/0793 | (2010.01) |
| A61K 35/30 | (2015.01) |
| G01N 33/50 | (2006.01) |

(52) U.S. Cl.
CPC ............ *C12N 5/0622* (2013.01); *A61K 35/30* (2013.01); *C12N 5/0619* (2013.01); *G01N 33/5058* (2013.01); *C12N 2501/11* (2013.01); *C12N 2501/115* (2013.01); *C12N 2501/155* (2013.01); *C12N 2501/385* (2013.01); *C12N 2501/41* (2013.01); *C12N 2506/02* (2013.01); *C12N 2533/52* (2013.01); *C12N 2533/90* (2013.01)

(58) Field of Classification Search
CPC ..... C12N 5/0619; C12N 5/0622; A61K 35/30
See application file for complete search history.

(56) References Cited

U.S. PATENT DOCUMENTS 5,830,651 A 11/1998 Cauley et al.
6,280,718 B1 8/2001 Kaufman et al.

8,809,052 B2 * 8/2014 Revel .................. C12N 5/0619
435/325
2004/0009593 A1 1/2004 Keirstead et al.
2005/0003544 A1 1/2005 Goldman et al.
2010/0003751 A1 1/2010 Revel et al.

FOREIGN PATENT DOCUMENTS

WO 01/68815 9/2001
WO 2008/026198 3/2008

OTHER PUBLICATIONS

Keirstead et al. The Journal of Neuroscience 25(19):4694-4705, May 2005.*
Palmer Neurobiology of Disease 37:3-12, 2010.*
Sylvester et al. Arch Surg. 139:93-99, 2004.
Communication Pursuant to Article 94(3) EPC Dated Jun. 16, 2011 From the European Patent Office Re.: Application No. 07790074.4.
Communication Pursuant to Article 94(3) EPC Dated Apr. 6, 2010 From the European Patent Office Re.: Application No. 07790074.4.
Reubinoff et al. "Neural Progenitors From Human Embryonic Stem Cells", Nature Biotechnology, 19: 1134-1140, Dec. 2001.
Zhang et al. "In Vitro Differentiation of Transplantable Neural Precursors From Human Embryonic Stem Cells", Nature Biotechnology, 19: 1129-1133, Dec. 2001.
Response Dated Jun. 7, 2011 to Communication Pursuant to Article 94(3) EPC of Dec. 14, 2010 From the European Patent Office Re.: Application No. 07790074.4.
Office Action Dated Apr. 27, 2011 From the Israel Patent Office Re. Application No. 197291 and Its Translation Into English.
Communication Pursuant to Article 94(3) EPC Dated Dec. 14, 2010 From the European Patent Office Re.: Application No. 07790074.4.
Supplementary Response Dated Nov. 18, 2010 to Communication Pursuant to Article 94(3) EPC of Apr. 6, 2010 From the European Patent Office Re.: Application No. 07790074.4.
Schuldiner et al. PNAS 97:21:11307-11312, 2000.
Konagaya et al. Biomaterials 32:992-1001,2010.
Response Dated Aug. 5, 2010 to Communication Pursuant to Article 94(3) EPC of Apr. 6, 2010 From the European Patent Office Re.: Application No. 07790074.4.
International Preliminary Report on Patentability Dated Apr. 16, 2009 From the International Bureau of WIPO Re.: Application No. PCT/IL2007/001026.
International Search Report Dated Aug. 5, 2008 From the International Searching Authority Re.: Application No. PCT/IL07/01026.
Written Opinion Dated Aug. 5, 2008 From the International Searching Authority Re.: Application No. PCT/IL07/01026.
Gerrard et al. "Differentiation of Human Embryonic Stem Cells to Neural Lineages in Adherent Culture by Blocking Bone Morphogenetic Protein Signaling", Stem Cells, 23: 1234-1241, 2005.
Itsykon et al. "Derivation of Neural Precursors From Human Embryonic Stem Cells in the Presence of Noggin", Molecular and Cellular Neuroscience, 30: 24-36, 2005.
Proceedings Further With the European Patent Application Pursuant to Rule 70(2) EPC Dated Dec. 21, 2009 From the European Patent Office Re.: Application No. 07790074.4.

(Continued)

*Primary Examiner* — Marcia S Noble
(74) *Attorney, Agent, or Firm* — Polsinelli PC; Ron Galant

(57) ABSTRACT

A method of generating neural and glial cells is provided. The method comprising growing human stem cells under conditions which induce differentiation of said human stem cells into the neural and glial cells, said conditions comprising the presence of retinoic acid and an agent capable of down-regulating Bone Morphogenic Protein activity.

4 Claims, 8 Drawing Sheets

(56) References Cited

OTHER PUBLICATIONS

Response Dated Feb. 18, 2010 to Proceedings Further With the European Patent Application Pursuant to Rule 70(2) EPC Dated Dec. 21, 2009 From the European Patent Office Re: Application No. 07790074.4.
Supplementary European Search Report and the European Search Opinion Dated Dec. 2, 2009 From the European Patent Office Re.: Application No. 07790074.4.
Chiba et al. "Noggin and Basic FGF Were Implicated in Forebrain Fate and Caudal Fate, Respectively, of the Neural Tube-Like Structures Emerging in Mouse ES Cell Culture", Experimental Brain Research, XP019328842, 163(1): 86-99, May 1, 2005. Abstract.
Finley et al. "BMP-4 Inhibits Neural Differentiation of Murine Embryonic Stem Cells", Journal of Neurobiology, XP009017895, 40(3): 271-287, Sep. 5, 1999. Abstract.
Goldman "Stem and Progenitor Cell-Based Therapy of the Human Central Nervous System", Nature Biotechnology, XP002556148, 23(7): 862-871, Jul. 2005.
Izrael et al. "Human Oligodendrocytes Derived From Embyonic Stem Cells: Effect of Noggin on Phenotypic Differentiation In Vitro and on Myelination In Vivo", Molecular and Cellular Neurosciences, XP005907285, 34(3): 310-323, Mar. 2, 2007.
Nistor et al. "Human Embryonic Stem Cells Differentiate Into Oligodendrocytes in High Purity and Myelinate After Spinal Cord Transplantation", GLIA, XP002556149, 49(3): 385-396, Feb. 2005. Abstract.
Okada et al. "Retinoic-Acid-Concentration-Dependent Acquisition of Neural Cell Identity During In Vitro Differentiation of Mouse Embryonic Stem Cells", Developmental Biology, XP004583563, 275(1): 124-142, Nov. 1, 2004. Abstract.
Park et al. "In Vitro and In Vivo analyses of Human Embryonic Stem Cell-Derived Dopamine Neurons", Journal of Neurochemistry, XP002556150, 92(5): 1265-1276, Mar. 2005. Abstract.
Sterneckert et al. "Bone Morphogenetic Proteins Produced by Cells Within Embryoid Bodies Inhibit Ventral Directed Differentiation by Sonic Hedgehog", Cloning and Stem Cells, XP002556151, 7(1): 27-34, Apr. 2005. Abstract.

* cited by examiner

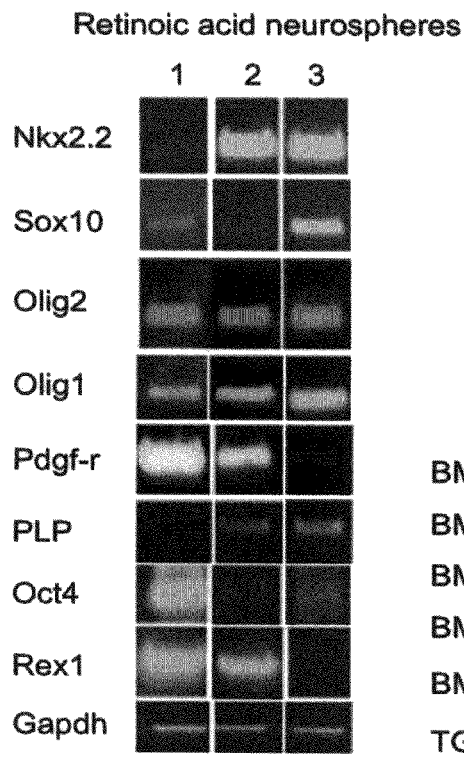
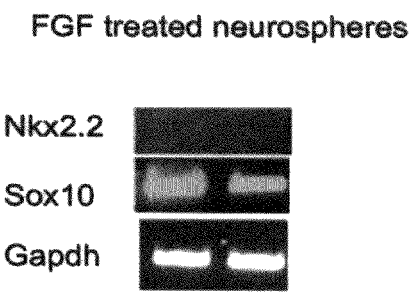
Fig. 1b
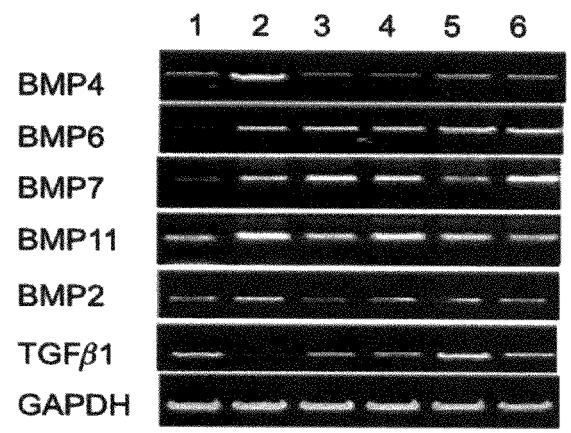
Fig. 1c
Fig. 1a
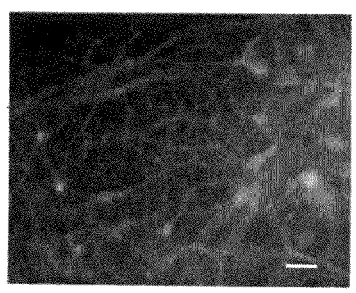
Fig. 1d
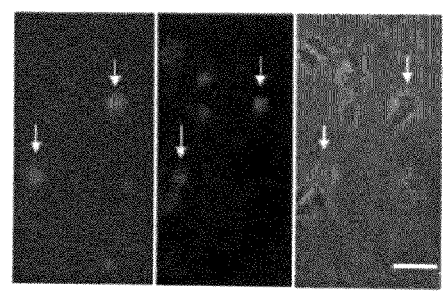
Fig. 1e

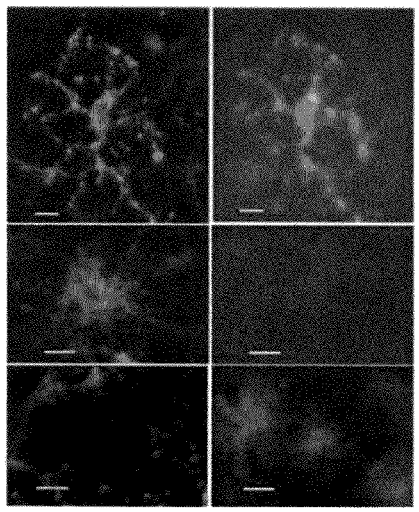
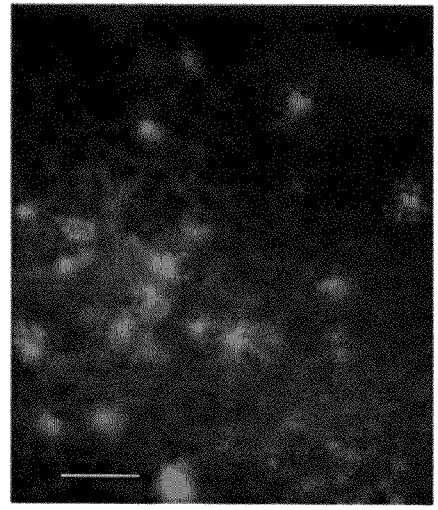
Fig. 2c
Fig. 2d
Fig. 2e
Fig. 2f
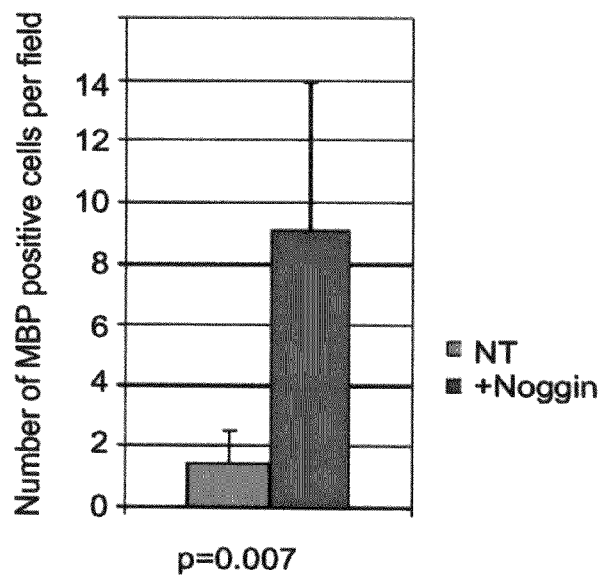
Fig. 2g

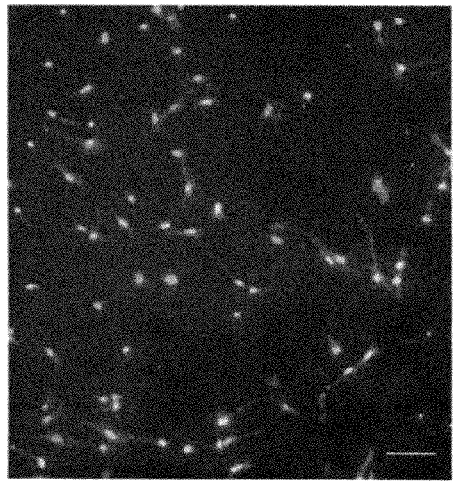
Fig. 3a
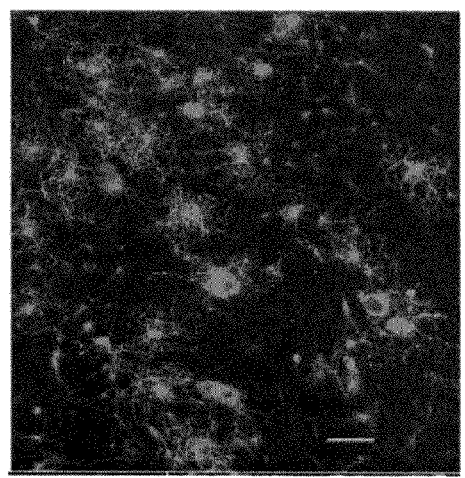
Fig. 3b
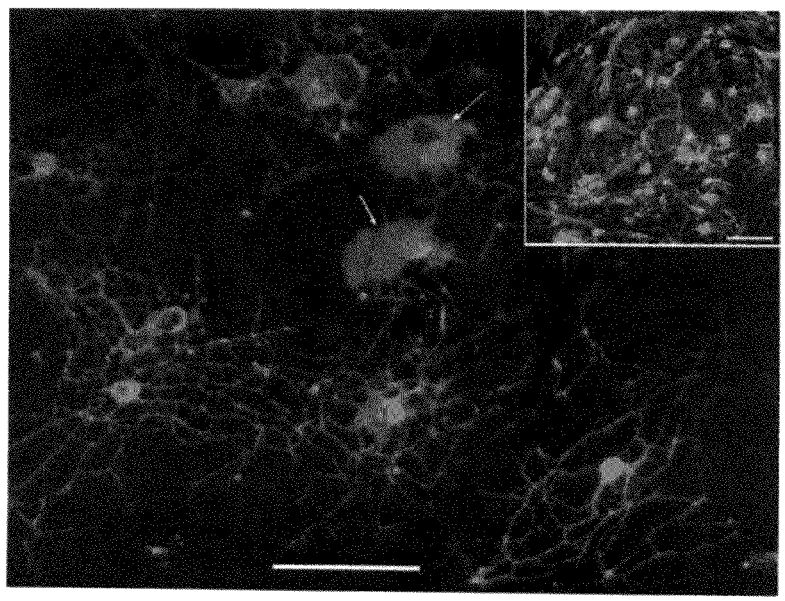
Fig. 3c
Fig. 3d

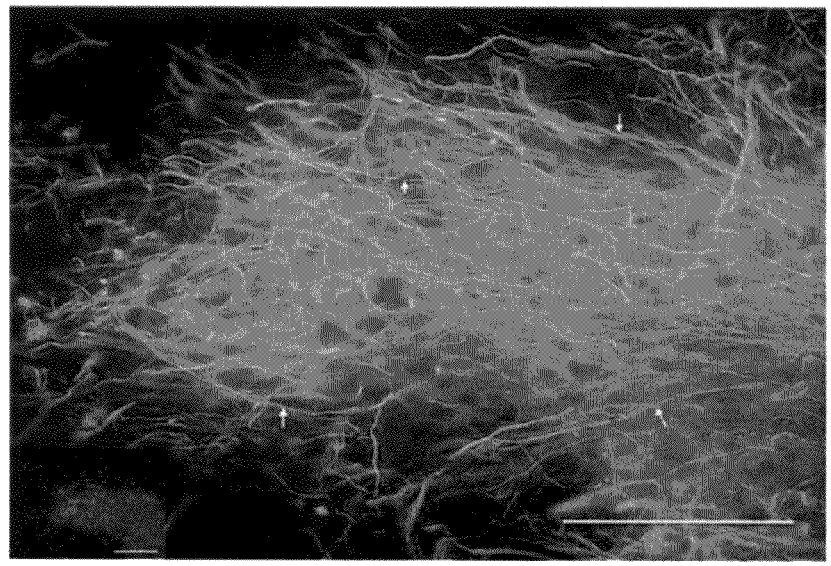
Fig. 5h　　　　　　　　Fig. 5c
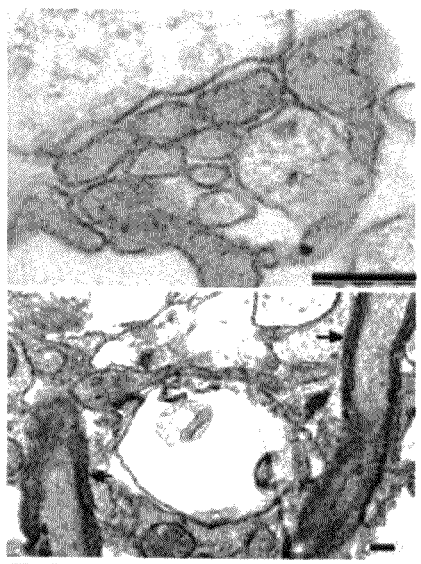
Fig. 5d
Fig. 5e
Fig. 5f

SEQUENCE LISTING

<160> NUMBER OF SEQ ID NOS: 28

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
ccttcatggt ggctttcttc                                               20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
ccaaagggtc tgaattctcg                                               20

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
agaactacca gaaacgagtg gg                                            22

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
cgctgtttgt gtttggcttg                                               20

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5 cggttctttacttt gatgac                                               20

<210> SEQ ID NO 6
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 6
gatagacagt actgaaccag c                                             21

<210> SEQ ID NO 7
<211> LENGTH: 21
<212> TYPE: DNA
<213> ORGANISM: Artificial sequence

```
<220> FEATURE:
<223> OTHER INFORMATION: Single strand DNA oligonucleotide

<400> SEQUENCE: 7
catttatgag gttatgaagc c                                             21

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
ccaccttatc atactcatcc ag                                            22

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
gcgactaaaa cccctaactg                                               20

<210> SEQ ID NO 10
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 10
ctgcaccaaa tgggtatgc                                                19

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
tgcctctcct tctgaacctt gg                                            22

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
gcgaaatctg ccaccagttg                                               20

<210> SEQ ID NO 13
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 13
cttgctgcag aagtgggtgg aggaa                                         25
```

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
ctgcagtgtg ggtttcgggc a                                    21

<210> SEQ ID NO 15
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 15
ttgcatccag tgttcccgat ttac                                 24

<210> SEQ ID NO 16
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 16
tgccagttaa attcggctac tacc                                 24

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
aaggaggcag tggcttcaag tc                                   22

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
cgctcaccag tcgcttcatc                                      20

<210> SEQ ID NO 19
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 19
ctatccacac tgtcaaacag gttg                                 24

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide -continued

```
<400> SEQUENCE: 20
tctgctggac tgagaagttt catc                                            24

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
ctgctcacct tcatgattgc                                                 20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
tgacttgcag ttgggaagtc                                                 20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
tgaaagccca catcctaacg                                                 20

<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
caagctatcc tcctgctttg g                                               21

<210> SEQ ID NO 25
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 25
gcctgttctc ctggggcttt gctgc                                           25

<210> SEQ ID NO 26
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 26
catccacctc acagatcgcc tacac                                           25

<210> SEQ ID NO 27
```

```
-continued

<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 27
cagcaacaat tcctggcgat ac                                              22

<210> SEQ ID NO 28
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 28
ggacagctgc tccaccttg                                                  19
```

METHODS OF GENERATING GLIAL AND NEURONAL CELLS AND USE OF SAME FOR THE TREATMENT OF MEDICAL CONDITIONS OF THE CNS

FIELD AND BACKGROUND OF THE INVENTION

The present invention relates to methods of generating glia cells such as oligodendrocyte like cells and the use of same for the treatment of medical conditions of the CNS.

Myelin, the fatty substance which encloses certain axons and nerve fibers, provides essential insulation, and enables the conductivity of nerve cells which transmit electrical messages to and from the brain.

Aberration in myelination can lead to several pathologies in the central nervous system. These include for example, autoimmune diseases (e.g Multiple Sclerosis), congenital leukodystrophies (e.g Pelizaeus-Merzbacher, vanishing white matter, adrenoleukodystrophy), infectious diseases (e.g. progressive multifocal leukoencephalopathy, postinflammatory demyelinated lesions), neurodegenerative diseases (e.g. multisystem degeneration), vascular diseases (vascular leukoencephalopathies, subcortical infarcts), congenital genetic defects (e.g. amyotrophic lateral sclerosis [ALS], Alzheimer disease, Parkinson disease) and brain and spinal cord trauma or injuries which are demyelinative and possibly neoplasms (e.g. oligodendrio-glioma).

Treatment of these pathologies may be effected by cell replacement therapies which eventually may allow achieving regional or even global repair of myelin as indicated by experiments in MBP-deficient shiverer mice (e.g., Yandava et al., 1999).

Oligodendrocytes extend as many as 50 processes which wrap around axons to form myelin sheaths. In vitro and in vivo, the development of oligodendrocytes proceeds in steps from neural stem cells to bipolar progenitors, then to multipolar precursor cells having several main processes which subsequently arborize and form the multiple branches of the mature cells (Rogister et al., 1999; Grinspan, 2002). Early oligodendrocytes precursors (OP) express the PDGF-receptor and later the specific O4 sulfatide marker of pre-oligodendrocytes which persists in ramified immature oligodendrocytes, then the maturating cells express galactocerebrosides (O1, GalC) and 2',3' cyclic nucleotide 3' phosphodiesterase (CNP), and at the final stage become postmitotic mature oligodendrocytes that synthesize the myelin membrane components such as proteolipid protein (PLP) and myelin basic protein (MBP).

Embryonic stem (ES) cell lines being amenable to mass culture and differentiation into specific cell lineages in vitro are a potential large scale source of oligodendrocytes for brain and spinal cord transplantation, which has been studied in experimental models using mouse ES cells (Liu et al., 2000; Zhang et al., 2004; Glaser et al., 2005; Zhang et al., 2006). For successful transplantation, the cells need the capacity to migrate into the CNS and, therefore, the appropriate stage of cell differentiation must be defined, since more differentiated oligodendrocytes migrate minimally but conversely the cells that migrate most are less likely to differentiate into mature myelinating cells (Warrington et al., 1993; Foster et al., 1995; Yandava et al., 1999).

Zhang et al (2004; 2006) describe a procedure which converts murine ES cells into highly branched and ramified oligodendrocytes and produces progenitor which upon implantation in shiverer mouse brain tissue, migrate and form dense arrays of myelinated nerve fibers. However, the need for human ES cells which can be converted and expanded into functional oligodendrocytes is yet far from being fulfilled.

The availability of human ES cell (huESC) lines, derived from supernumerary human IVF blastocysts, provides a potential large scale source of human oligodendroglial and neural precursor cells that could be used in clinical settings to treat a variety of severe human neurological diseases, congenital or acquired. Neural stem cells from brain or spine of aborted human fetuses may be another source of neural stem cells, but preparing engraftable quantities of cells from fetal or adult human brain presents many problems (Goldman, 2005). While human fetal brain cells can differentiate into ramified mature oligodendrocytes (Zhang et al., 2000), most studies show that fetal brain precursor cells lose their ability to produce oligodendrocytes upon expansion (Chandran and Compston, 2005). Therefore, the use of laboratory-established huESC lines that can be expanded in relatively large scale cultures, would be highly advantageous to prepare the grafts.

Previous attempts to use human ES cells lines for deriving oligodendrocytes have yielded only partial success. A first study described the preparation of neural tube-like rosettes which were expanded by bFGF into neurospheres and eventually transplanted into the third ventricule of newborn mice brain (Zhang et al., 2001). In this work only elongated bipolar $O4^+$ OPC were obtained and no myelination was shown following transplantation. Another study (Reubinoff et al., 2001) produced neurospheres from huESC with EGF and bFGF, and showed multipolar $O4^+$ cells with a few processes, as well as CNP-positive cells after transplantation but without evidence for myelination. A further study, with huESC-derived neurospheres that were produced with bFGF and noggin yielded $O4^+$ precursors but no ramified or mature cells, and no transplantation was done (Itsykson et al., 2005).

The inability of neurons in the mammalian central nervous system (CNS) to regenerate axons is due to inhibitory influences by glial cells of the CNS, which prevent the re-activation of growth promoting genes. However, axonal regeneration occurs in the peripheral nervous system (PNS). Retinoic acid-mediated signal transduction is known to induce these regenerative processes in the PNS. Retinoic acid (RA) is one of the active forms of vitamin A and is involved in life maintaining processes such as reproduction, embryonic development, vision, growth, cellular differentiation and proliferation, tissue maintenance and lipid metabolism. By activating a number of regulatory genes and signaling molecules, retinoic acid plays a crucial role during the development of the vertebrate nervous system. RA also initiates cell development of immature blood cells. One of the many medical uses of RA is for the treatment of Acute Myeloid Leukemia. Administration of RA causes the highly proliferative immature blood cells typical of this disease, to differentiate and develop into functional cells.

Because of its known functions, retinoic acid was used to induce neural differentiation and neurospheres in murine ES cells (Bain et al., 1995; Liu et al., 2000). Following this approach (Nistor et al., 2005), retinoic acid was used for the induction of neural-lineage cells from HuESC, in concurrence with preferential selection of oligodendrocyte-lineage cells by media components and matrigel adherence. Although "high purity functional oligodendrocytes from huESC" were claimed, no well differentiated, highly branched and ramified oligodendrocytes were produced, and after transplantation to spinal cord of shiverer mouse, there were only small patches of MBP-positive cells with no evidence for extended areas of remyelination and no myelinated nerve fibers of at least 100 μm.

All the described attempts to produce fully differentiated and mature oligodendrocytes from human ES cells convey that procedures which have been successful with murine ES cells cannot be extrapolated to human ES cells. Thus, the need for production of fully differentiated and mature human oligodendrocytes still exists.

For this purpose, key genes, encoding transcription factors which are obligatory for the development of the oligodendrocyte lineage need to be studied, in order to define the agents that are needed to convert huESC into oligodendrocytes, and the agents which delay this process, and need to be inhibited. For example, Bone Morphogenetic Proteins (BMPs) are group of growth factors known for their ability to induce the formation of bone and cartilage. Signal transduction through BMPs, is important for the development of the heart, central nervous system, and cartilage, as well as post-natal bone development. Noggin, which binds to members of the TGF-β superfamily, plays a crucial role in bone development and neurulation, by regulating the functions of BMP's. For example, it was found that noggin counteracts the effect of BMPs, which in turn were found to inhibit oligodendrocyte development from rat fetal brain (Mehler et al., 1997; Mehler et al., 2000).

There is thus a widely recognized need for producing fully differentiated, and mature oligodendrocytes propagated and expanded from human ES cells, that addresses these deficiencies.

SUMMARY OF THE INVENTION

According to one aspect of the present invention there is provided a method of generating neural and glial cells, the method comprising growing human stem cells under conditions which induce differentiation of the human stem cells into the neural and glial cells, the conditions comprising the presence of retinoic acid and an agent capable of down-regulating Bone Morphogenic Protein activity.

According to another aspect of the present invention there is provided a method of generating glial cells, the method comprising: (a) growing human stem cells in the presence of retinoic acid, under conditions which allow formation of neurospheres; and (b) contacting the neurospheres with an agent capable of down-regulating Bone Morphogenic Protein activity thereby generating the glial cells.

According to yet another aspect of the present invention there is provided a method of generating oligodendrocytes, the method comprising: (a) growing human stem cells in the presence of retinoic acid under conditions which allow the formation of neurospheres; and (b) contacting the neurospheres with an agent capable of down-regulating Bone Morphogenic Protein activity thereby generating the oligodendrocytes.

According to still another aspect of the present invention there is provided a method of generating neurons, the method comprising: (a) growing human stem cells in the presence of retinoic acid under conditions which allow the formation of neurospheres; and (b) contacting the neurospheres with an agent capable of down-regulating Bone Morphogenic Protein activity under conditions which allow neuronal cells generation, the conditions comprising Sonic Hedgehog (Shh), thereby generating the neurons.

According to an additional aspect of the present invention there is provided an isolated oligodendrocyte cell generated according to any of the above methods.

According to yet an additional aspect of the present invention there is provided an isolated astrocyte cell generated according to any of the above methods.

According to still an additional aspect of the present invention there is provided an isolated neuronal cell generated according to any of the above methods.

According to a further aspect of the present invention there is provided an isolated population of cells comprising human cells wherein, (i) at least N % of the human cells comprise at least one mature oligodendrocyte phenotype; and (ii) at least M % of the human cells comprise at least one stem cell phenotype.

According to yet a further aspect of the present invention there is provided a method of treating a medical condition of the CNS in a subject-in-need thereof, the method comprising administering to the subject a therapeutically effective amount of the cells of the present invention, thereby treating the medical condition of the CNS.

According to still a further aspect of the present invention there is provided use of the cells of the present invention, for the manufacture of a medicament identified for treating a medical condition of the CNS.

According to still a further aspect of the present invention there is provided a pharmaceutical composition comprising as an active ingredient the cells of the present invention and a pharmaceutically acceptable carrier or diluent.

According to further features in preferred embodiments of the invention described below, the human stem cell is a human embryonic stem cell.

According to still further features in the described preferred embodiments the oligodendrocyte comprises a precursor oligodendrocyte phenotype.

According to still further features in the described preferred embodiments the precursor oligodendrocyte phenotype comprises cell migration.

According to still further features in the described preferred embodiments the precursor oligodendrocyte phenotype comprises cell expansion.

According to still further features in the described preferred embodiments the cell expansion comprises in vitro cell expansion.

According to still further features in the described preferred embodiments the cell expansion comprises in vivo cell expansion.

According to still further features in the described preferred embodiments the precursor oligodendrocyte phenotype comprises a marker expression selected from the group consisting of PDGF-receptor, O4 sulfatide marker, galactocerebrosides (O1, GalC), Nkx2.2, Sox10, oligodendrocyte specific protein (OSP), myelin-associated glycoprotein (MAG), 2',3'-cyclic nucleotide-3'-phosphodiesterase (CNP), glutathione-S-transferase (GST), adenomatous polyposis coli (APC); myelin oligodendrocyte glycoprotein (MOG), CNPase, MOSP and Oligodendrocyte NS-1.

According to still further features in the described preferred embodiments the precursor oligodendrocyte phenotype comprises a cell morphology selected from the group consisting of round or elongated, bipolar or multipolar shape.

According to still further features in the described preferred embodiments the oligodendrocyte comprises a mature oligodendrocyte phenotype.

According to still further features in the described preferred embodiments the mature oligodendrocyte phenotype comprises in vivo and in vitro myelin production.

According to still further features in the described preferred embodiments the glial cells comprise astrocytes.

According to still further features in the described preferred embodiments the glial cells comprise mature oligodendrocytes which comprise a mature oligodendrocyte phenotype.

According to still further features in the described preferred embodiments the mature oligodendrocyte phenotype comprises a mature oligodendrocyte marker expression.

According to still further features in the described preferred embodiments the mature oligodendrocyte marker is selected from a group consisting of PLP, MBP, MAG and MOG.

According to still further features in the described preferred embodiments the mature oligodendrocyte phenotype comprises a mature oligodendrocyte structural phenotype.

According to still further features in the described preferred embodiments the mature oligodendrocyte structural phenotype is branched and ramified.

According to still further features in the described preferred embodiments the method further comprising forming stem cell aggregates prior to step (a).

According to still further features in the described preferred embodiments the conditions further comprise culturing the stem cells in the presence of a growth factor.

According to still further features in the described preferred embodiments the growth factor is selected from a group consisting of bFGF and EGF.

According to still further features in the described preferred embodiments a concentration of the EGF comprises a range of 10-40 ng/ml.

According to still further features in the described preferred embodiments the conditions further comprise culturing the neurospheres on an adherent substrate following step (a).

According to still further features in the described preferred embodiments the conditions further comprise culturing the neurospheres on a cationic substrate following step (a).

According to still further features in the described preferred embodiments the adherent substrate comprises a substrate selected from the group consisting of a matrigel and an extracellular matrix component.

According to still further features in the described preferred embodiments the extracellular matrix component is selected from the group consisting of collagen, laminin and fibronectin.

According to still further features in the described preferred embodiments the cationic substrate is selected from a group consisting of poly D/L lysine and Polyomithine FN.

According to still further features in the described preferred embodiments a concentration of the retinoic acid comprises a range of 1-50 µM.

According to still further features in the described preferred embodiments the retinoic acid is selected from the group consisting of retinoic acid, retinol, retinal, 11-cis-retinal, all-trans retinoic acid, 13-cis retinoic acid and 9-cis-retinoic acid.

According to still further features in the described preferred embodiments the step (a) is effected for 20-30 days.

According to still further features in the described preferred embodiments the step (b) is effected for 6-10 days.

According to still further features in the described preferred embodiments the agent is selected from the group consisting of noggin, chordin, chordin like BMP inhibitor (CHL2), Neuralin, follistatin, GDF3, Crossveinless-2 (hCV-2), Ectodin, Sclerostin, connective tissue growth factor (CTGF), BMP-3, Inhibin, Cerberus, Coco, PRDC, DAN, USAG1, Twisted gastrulation (TSG), gp130 signaling cytokines and gremlin.

According to still further features in the described preferred embodiments the agent is noggin.

According to still further features in the described preferred embodiments a concentration of the noggin comprises a range of 10-100 ng/ml.

According to still further features in the described preferred embodiments step (b) is effected at least in part in the absence of growth factors.

According to still further features in the described preferred embodiments step (b) is effected in the presence of laminin and vitamin C.

According to still further features in the described preferred embodiments the method further comprising:
dissociating cells of the neurospheres; and
passaging the dissociated cells; following step (a) and/or concomitantly with step (b).

According to still further features in the described preferred embodiments the passaging is effected every 8-10 days.

According to still further features in the described preferred embodiments the method further comprising isolating a glial cell subpopulation of interest following step (b).

According to still further features in the described preferred embodiments the method further comprising isolating the oligodendrocytes following step (b).

According to still further features in the described preferred embodiments the method further comprising isolating the neurons following step (b).

According to still further features in the described preferred embodiments the medical condition is selected from the group consisting of autoimmune diseases, Guillan-Barre syndrome or congenital leukodystrophies, adrenoleukodystrophies, Pelizaeus-Merzbacher, Charcot-Marie-Tooth, Krabbe or Alexander disease, vanishing white matter syndrome, progressive multifocal leukoencephalopathy, infectious demyelinating diseases, postinflammatory demyelinated lesions, neurodegenerative diseases, multisystem degeneration, vascular diseases, ischemic white matter damage, vascular leukoencephalopathies, subcortical infarcts, brain trauma, spinal cord trauma, demyelinative injury, neoplasms and oligodendrio-glioma.

According to still further features in the described preferred embodiments the cells comprise oligodendrocytes and the medical condition is associated with insufficient myelination According to still further features in the described preferred embodiments the cells comprise neuronal cells and the medical condition is selected from the group consisting of motor neuron diseases, progressive muscular atrophy (PMA), spinal muscular atrophy (SMA), progressive bulbar palsy, pseudobulbar palsy, primary lateral sclerosis, neurological consequences of AIDS, amyotrophic lateral sclerosis (ALS), Alzheimer's disease, developmental disorders, epilepsy, multiple sclerosis, neurogenetic disorders, Parkinson's disease, neurodegenerative disorders, stroke, spinal cord injury and traumatic brain injury.

According to still further features in the described preferred embodiments the cells comprise astrocytes and the medical condition is selected from the group consisting of Alexander disease, epilepsy, Alzheimer's disease, spinal cord injury, traumatic brain injury and neurogenesis deficiencies.

According to still a further aspect of the present invention there is provided a method of determining an effect of treatment on neural cell functionality, the method comprising: (a) subjecting cell generated according to any of the above methods to the treatment; and (b) determining at least one of a structural or functional phenotype of the treated cell as compared to an untreated cell, thereby determining an effect of the treatment on neural cell functionality.

According to still further features in the described preferred embodiments the treatment comprises a treatment with a drug.

According to still further features in the described preferred embodiments the treatment comprises a treatment with a condition.

According to still further features in the described preferred embodiments the condition is selected from the group consisting of an electrical treatment and an irradiation treatment.

The present invention successfully addresses the shortcomings of the presently known configurations by providing novel methods of generating glia cells and in particular oligodendrocytes and methods of using such cells for the treatment of medical conditions of the CNS.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 *a* shows RT-PCR images depicting the gene expression profile of retinoic acid treated neurospheres at the end of step R of the treatment (10 μM Retinoic acid treatment; lane 1) and at the end of step S (Suspension culture, where neurospheres are allowed to ripen), without noggin (lane 2) or with noggin (50 ng/ml Noggin-Fc chimera; lane 3). Note that retinoic acid and noggin are both needed in order to induce the expression of genes characterizing oligodendrocyte development: Nkx2.2, Sox10, Olig2, Olig1. FIG. 1 *b* shows RT-PCR images depicting the gene expression profile of FGF treated neurospheres (left lane), and neurospheres additionally treated with thyroid hormone (triiodothyronin, T3; right lane). Note that this procedure, which was found to be successful for murine ES cell differentiation into oligodendrocytes, does not appear to induce Nkx2.2 in human ES cells. FIG. 1 *c* shows RT-PCR images depicting the expression profile of Bone Morphogenetic Protein (BMP) genes by human ES cells, before (lane 1) and after (lane 2) step R (10 μM Retinoic acid treatment), after step S (Suspension culture, where neurospheres are allowed to ripen), with noggin (so ng/ml Noggin-Fc chimera; lane 3) or without noggin (lane 4), after step M (adherence to matrigel-coated plates of neurospheres from cultures without noggin at step S; lane 5), same after step F 1 (5 ng/ml EGF and bFGF, 50 ng/ml Noggin-Fc chimera, 1 μg/ml mouse laminin, and 50 μg/ml Vit C) and step F2 (same but without EGF, bFGF; lane 6). Note expression panel shows several BMP genes (inhibitors of oligodendrocyte development) are induced by retinoic acid treatment and some of them increase further during the differentiation procedure. Noggin (a BMP family antagonist), is required to counteract BMPs induction by RA. FIG. 1 *d* is a fluorescent light micrograph depicting immunostained neurospheres during step M (adherence to matrigel). Immunostaining shows that after only 4 days in step M the outgrowth from the neurospheres contain neurons (immunostained for neuronal tubulin-βIII) and small cells stained for the oligodendrocyte-specific marker O4. Size bar, 20 μm. FIG. 1 *e* is a fluorescent light micrograph depicting the O4 positive cells (indicated by arrows) at the end of step M (after 9 days; panel 1). Cells show positive immunostaining for the astrocytes lineage marker GFAP (panel 2) and are small unipolar cells (panel 3), which identifies them as glial progenitor cells. Size bar, 20 μm. FIG. 1 *f* is a fluorescent light micrograph depicting neurospheres after step F2 (done on matrigel, without GF but with noggin, added only at this step, for 6 days). Immunostaining for PDGF Receptor-α shows the presence of elongated bipolar oligodendrocyte progenitors (OP). Immunostaining for the oligodendrocyte-specific marker O4 shows differentiated highly branched $O_4^+$ oligodendrocytes. Size bar, 20 μm. FIGS. 1 *g-h* are fluorescent light micrographs depicting the same culture described in FIG. 1 *f*, following 10 days without GF, without (FIG. 1 *g*) and with (FIG. 1 *h*) noggin. Immunostaining shows that without noggin there are mainly $O_4^+$ bipolar precursors, whereas with noggin there are numerous highly branched well-differentiated oligodendrocytes. Size bar, 100 μm.

FIGS. 2 *a-b* are fluorescent light micrographs showing the same immunostained cells after step F2 (10 days without GF) with noggin added only at steps F 1, F2, and stained for MBP (FIG. 2 *a*), or double-stained for O4 and MBP (FIG. 2 *b*). FIGS. 2 *c-f* are fluorescent light micrographs of different MBP-positive cells immunostained for MBP and O4. FIG. 2 *c* shows cells which are MBP and O4 positive. FIGS. 2 *d-e* show that while some cells are still only O4 positive (FIG. 2 *d*) some have matured further to the $MBP^+$, $O4^-$ phenotype (FIG. 2 *e*; Size bar for. FIGS. 2 *c-e*, 20 μm). FIG. 2 *g* is a bar graph depicting quantitation assessment of the number of $MBP^+$ cells in fields (such as in FIG. 2*f*, Size bar, 100 μm). Note the strong stimulation caused by noggin as compared to cultures without noggin (NT).

FIGS. 3 *a-d* are fluorescent light micrographs showing that human ES cell-derived dissociated neuroglial sphere cells (huEs-NSc) cells can be dissociated by trypsin, expanded with EGF and bFGF on poly-D-lysine coated plates and then differentiated into large mature oligodendrocytes. FIG. 3 a depicts cells grown in culture conditions as described in condition 3 in Table 1, Example 1 in the Examples section after step D3 (Expansion of huEs-NSc) with noggin. The cells were starved of GF for 1 day, trypsinized and plated for 18 hours before fixation and immunostaining for O4 and dapi. Comparison with dapi-stained nuclei shows a homogenous population of bipolar precursors. Size bar 100 μM. FIGS. 3 b-c depict the accumulation of multibranched ramified oligodendrocytes in the same culture described in FIG. 3 a (Passage 3) after differentiation step F2, 10 days without GF but with noggin. Higher magnification (FIG. 3 c) shows the branching network and the development of flat and broad membranes (arrows). Size bar 100 μm. FIG. 3 d depicts the same culture described in FIGS. 3 a-c, immunostained for the O1 marker denoting mature oligodendrocytes and for GFAP to visualize astrocytes. Size bar 100 μm.

FIG. 4 a-d,g are fluorescent light micrographs depicting sections of brain implanted with HuES-NScs, treated (FIGS. 4 b-d,g), or not treated (FIG. 4 a) with noggin for 9 days at step D3 (passage step, as described in Table 3). FIG. 4 a-b are sections of the cortex. Note more MBP stained fibers were observed with HuES-NSc treated with noggin (FIG. 4b), and long fibers were seen (indicated by arrows). FIG. 4 e is a bar graph showing number of MBP fibers in cells cultured with or without noggin. Note increased number of MBP fibers/field with noggin. FIG. 4 c depicts MBP stain of a section field that includes part of the ventricule (v), visualizing the synthesis of MBP along the ventricule walls (as indicated by an arrow). Arrowhead demonstrates how the cells migrated into the brain parenchyma where MBP$^+$ fibers of various lengths are observed over a large area. FIG. 4 g shows the same field stained for Human Nuclear Antigen (HNA, green) confirming the human origin of the myelinating cells. Size bar 100 μm. FIG. 4 d depicts an adjacent area in the striatum, stained for MBP (red) and nuclear dapi. Note a dense cluster of MBP stained fibers in the center, with arrays of parallel fibers (as indicated by an arrowhead) and long fibers (as depicted by an arrow). Size bar 100 μm.

FIGS. 5 a-c depict a brain section following implantation of HuES-NSc, and stained for MBP (FIG. 5 a, c) and dapi (FIG. 5 b), as described in FIG. 4a. FIG. 5 a depicts MBP stained fibers (as indicated by arrows), in an extended area of the entorhinal cortex, two weeks after implantation in the hippocampal region. FIG. 5 b depicts cell nuclei stained with dapi. Size bar 100 μm. FIG. 5 c shows, in higher magnification, dense arrays of MBP-stained fibers, some of extended length (indicated by arrows). FIG. 5 h is the same section of FIG. 5 c, stained with nuclear dapi. Size bar 100 μm. FIGS. 5 d-f are electron micrographs of sections in the corpus callosum region, depicting nerves. FIG. 5 d depicts dysmyelinated nerves in the Shiverer brain, whereas in brain slices transplanted by huES-NS cells treated with noggin (as above), compact myelin with major dense lines is clearly observed (as indicated by arrows in FIGS. 5 e and 5 f), indicating myelinated nerve fibers are formed following transplantation. Size bars 0.2 μm in FIG. 5 d-e, and 0.1 μm in FIG. 5f. FIG. 5 g depicts bar graphs showing, as indicated, measurements of the extent of MBP stain (by color-specific integrated optical density) and mean length of MBP$^+$ fibers, in similar transplantation of cells treated, or not treated, by noggin (p<0.004 for both).

DESCRIPTION OF THE PREFERRED EMBODIMENTS

Figure 1F:
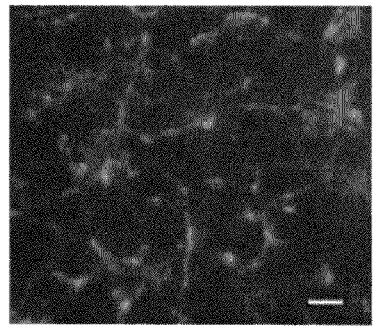
FIGS. 1 *a-h* depict the early steps (as described in Example 1 in the Examples section, and summarized in Table 1, condition 1) in obtaining neuroglial sphere cells (NSc) from human ES cells, and their differentiation into $O_4^+$ oligodendrocytes in response to noggin.

The present invention is of methods of deriving neural cells, such as oligodendrocytes from human stem cells, and the use of same in treating medical conditions of the CNS.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The main function of oligodendrocytes is the myelination of nerve cells. The myelin sheath serves as insulation, resulting in decreased ion leakage, lower capacitance of the cell membrane and as a result allows salutatory nerve conduction (i.e. the fast propagation of neuroelectrical impulses). The myelin sheaths and several of its protein components play essential roles in protection of neurons against disintegration and death. Diseases that result in injury of oligodendroglial cells include demyelinating diseases such as multiple sclerosis, infectious or ischemic demyelinating diseases and various types of inherited or acquired leukodystrophies. Information about functions of myelin and diseases caused by alterations of myelin can be found in Lazzarini et al, eds (2004) Myelin biology and disorders, Elsevier Academic Press, San Diego, Calif.).

In the past few years, research on stem cells has expanded greatly as a tool to develop potential therapies to treat incurable neurodegenerative diseases.

Previous attempts to use human embryonic stem cell (huESC) lines for deriving oligodendrocytes have yielded only partial success. A first study described the preparation of neural tube-like rosettes which were expanded by bFGF into neurospheres and eventually transplanted into the third ventricule of newborn mice brain (Zhang et al., 2001). However, only elongated bipolar O4$^+$ OPC were obtained and no myelination was shown following transplantation.

Another study (Reubinoff et al., 2001) produced neurospheres from huESC with EGF and bFGF, and showed multipolar O4$^+$ cells with a few processes, as well as CNP-positive cells after transplantation but without evidence for myelination. A further study, with huESC-derived neurospheres that were produced with bFGF and noggin yielded O4+ precursors but no ramified or mature cells, and no transplantation was done (Itsykson et al., 2005).

In yet another study, retinoic acid was used to induce neural differentiation and neurosphere production from murine ES cells (Bain et al., 1995; Liu et al., 2000). Following this approach (Nistor et al., 2005), retinoic acid was used for the induction of neural-lineage cells from huESC, in concurrence with preferential selection of oligodendrocyte-lineage cells by media components and matrigel adherence. Although "high purity functional oligodendrocytes from huESC" were claimed, no well differentiated, highly branched and ramified oligodendrocytes were produced, and after transplantation to spinal cord of shiverer mouse, there were only small patches of MBP-positive cells with no evidence for extended areas of remyelination and no myelinated nerve fibers of at least 100 μm.

All the described attempts to produce fully differentiated and mature oligodendrocytes from human ES cells convey that procedures which have been successful with murine ES cells cannot be extrapolated to human ES cells. Thus, the need for ex vivo or in vivo production of fully differentiated, and mature oligodendrocytes propagated and expanded from human ES cells is still unmet.

While reducing the present invention to practice, the present inventors have uncovered that incubation of human stem cells with retinoic acid and followed by incubation with noggin can be used for deriving myelinating oligodendrocytes. Such cells can be used with great convenience and accessibility in the treatment of medical conditions associated with demyelination.

As is described herein below and in the Examples section which follows, the present inventors have uncovered, through laborious experimentation, a novel procedure for generating oligodendrocytes as well as neurons from human embryonic stem cells. The general guidelines of the methods of the present invention are further provided in Examples 1-3 and 5 of the Examples section which follows.

Briefly, incubation of ES cell aggregate suspension culture in the presence of retinoic acid causes the formation of neurospheres. Spheres are allowed to ripen and outgrow on an adherent substrate. Spheres are dissociated and cells are allowed to expand through several passages in the presence of Noggin (with bFGF and EGF at the indicated concentrations). Differentiation in the presence of Noggin after removal of growth factors elicits the generation of oligodendrocytes (mature as well as expandable precursosrs). Such cells may be in vitro passaged and expanded while retaining their ability to myelinate in vitro and in vivo.

Thus, it is the combination of RA treatment followed by addition of noggin that is essential for formation of mature oligodendrocytes, which produce myelin proteins such as Myelin Basic Protein (MBP). In fact the present inventors have uncovered that noggin acts to counteract Bone Morphogenic Proteins (BMPs), formed in response to retinoic acid and which prevents the full differentiation oligodendrocytes.

Oligodendrocyte precursors generated according to the teachings of the present invention, were transplanted to shiverer mouse brains (in which an extensive deletion in the MBP gene exists, preventing any MBP formation). Immunostaining for MBP showed that the transplanted cells of the present invention have the capacity to myelinate endogenous neurons in vivo (see Example 4). Electron microscopy demonstrates the generation of thick sheaths of compact myelin with major dense lines contrasting with the dysmyelinated nerves seen in the non-transplanted shiverer mouse brain. These results substantiate the use of the cells of the present invention as reparative medicine of various medical conditions of the CNS and in particular of demyelinating disease.

Thus, according to one aspect of the present invention there is provided a method of generating neuronal and glial-like cells.

The phrase "glial cells", also termed interchangeably herein as "glia", are non-neuronal cells that provide support and nutrition, maintain homeostasis, form myelin, and participate in signal transmission in the nervous system. Examples of glial cells of the present invention include but are not limited to astrocytes and oligodendrocytes (mature and precursor, as further described herein below).

As used herein the term "oligodendrocyte" refers to both oligodendrocyte precursor cells (OPCs) and mature well-differentiated oligodendrocytes. The function of these cells is described above. Mature oligodendrocytes may be distinguished from OPCs both by structural and functional phenotypes.

Examples of a mature oligodendrocyte functional phenotype include, but are not limited to one or more, marker expression such as proteolipid protein (PLP) and MBP expression, myelin-associated glycoprotein (MAG), myelin oligodendrocyte glycoprotein (MOG), in addition to galactocerebrosides (O1, GalC).

Examples of mature oligodendrocyte structural phenotype include, but are not limited to, a branched and ramified phenotype and formation of myelin membranes.

Examples of an OPC functional phenotype include, but are not limited to, mitotic (i.e. that can divide and be expanded for three or more passages in culture) and migratory capacities as well as the potential to differentiate into a myelinating phenotype to effect myelination in vivo and in vitro.

Examples of OPC marker expression include, but are not limited to, PDGF-receptor, O4 sulfatide marker, Nkx2.2, Sox10, Olig1/2, oligodendrocyte specific protein (OSP), 2',3'-cyclic nucleotide-3'-phosphodiesterase (CNP), adenomatous polyposis coli (APC); NG2 (Chondroitin sulfate proteoglycan), A2B5, GD3 (ganglioside), nestin, vimentin and E- or PSA-NCAM.

Examples of OPC structural phenotype include, but are not limited to elongated, bipolar or multipolar morphology. For example only OPCs, but not mature oligodendrocytes and astrocytes, incorporate bromodeoxyuridine (BUdR), a hallmark of mitosis.

As used herein the term "astrocytes" also termed astroglia refers to the cells which anchor neurons to their blood supply. Generally, astrocytes regulate the external chemical environment of neurons by removing excess ions, notably potassium, and recycling neurotransmitters released during synaptic transmission. Astrocytes may be the predominant "building blocks" of the blood-brain barrier. Astrocytes may regulate vasoconstriction and vasodilation by producing substances such as arachidonic acid, whose metabolites are vasoactive.

Astrocytes of the present invention refer to both protoplasmic and fibrous astrocytes. Protoplasmic astrocytes have short, thick, highly branched processes and are typically found in gray matter. Fibrous astrocytes have long, thin, less branched processes and are more commonly found in white matter.

Astrocytes of the present invention are characterized by expression of one or more marker, glial fibrillary acidic protein (GFAP), S100 beta, glutamine sythetase, GLAST or GLT1 and have at least one astrocytic phenotype selected from a structural astrocytic phenotypes and a functional astrocytic phenotype. Thus, astrocytic structural phenotypes include a round nucleus, a "star shaped" body and many long processes that end as vascular foot plates on the small blood vessels of the CNS. Further examples of structural astrocytic phenotypes may be found in the following materials: Reynolds and Weiss, Science (1992) 255:1707-1710; Reynolds, Tetzlaff, and Weiss, J. Neurosci (1992) 12:4565-4574; and Kandel, et al., Principles of Neuroscience, third ed. (1991), Appleton & Lange, Norwalk, Conn. These structural phenotypes may be analyzed using microscopic techniques (e.g. scanning electro microscopy). Antibodies or dyes may be used to highlight distinguishing features in order to aid in the analysis. Other glial cells which may be generated in accordance with the teachings of the present invention include, but are not limited to, olfactory-type glia and myelinating or non-myelinating Schwann cells.

As used herein the phrase "neuronal cells" refers to the polar cells of the vertebrate nerve system which are specialized for the transmission of nerve impulses. Such cells typically display neuronal cell structure and express at least one neuronal marker. Examples of such markers include, but are not limited to neuronal and dopaminergic markers examples of which include, but are not limited to, Peripherin, Choline Acetyltransferase [ChAT], Chromogranin A, DARPP-32, GAD65, GAD67, GAP43, HuC, HuD, Alpha internexin, MAPS, MAP-2 A&B, Nestin, NeuN, Neurofilament L, M, H, Neuron-Specific Enolase (gamma-NSE), P75, low affinity NGF receptor, Peripherin, PH8, Protein Gene Product 9.5 (PGP9.5), Serotonin Transporter (SERT), Synapsin, Tau, Thy-1, TrkA, Tryptophan Hydroxylase (TRH) Beta III Tubulin, TUC-4 (TOAD/Ulip/CRMP) Tyrosine hydroxylase (TH) Vanilloid Receptor Like Protein 1 (VRL-1), Vesicular GABA Transporter (VGAT) Vesicular Glutamate Transporter 1 (VGLUT1; BNPI) and VGLUT2 (all available at Chemicon/Millipore, Temecula, Calif.).

Oligodendrocytes, neurons and other glial cells of this aspect of the present invention are generated by growing human stem cells under conditions which induce the differentiation of the human stem cells into the neuronal and glial cells. These conditions comprise the presence of retinoic acid and an agent capable of down-regulating Bone Morphogenic Protein (BMP) activity.

As used herein the phrase "stem cells" refers to cells which are capable of differentiating into other cell types (i.e., neuronal or glial cells as described herein) having a particular, specialized function (i.e., "fully differentiated" cells) or self-renew while remaining in an undifferentiated state. Examples of stem cells which can be used in accordance with this aspect of the present invention include, but are not limited to, embryonic stem cells as well as fetal or adult stem cells (e.g., mesenchymal). According to currently known preferred embodiment of the present invention, the stem cells are embryonic stem cells.

It will be appreciated that undifferentiated stem cells are of a distinct morphology, which is clearly distinguishable from differentiated cells of embryo or adult origin by the skilled in the art. Typically, undifferentiated stem cells have high nuclear/cytoplasmic ratios, prominent nucleoli and compact colony formation with poorly discernable cell junctions. Additional features of undifferentiated stem cells are further described hereinunder.

The stem cells can be obtained using well-known cell-culture methods.

For example, human embryonic stem cells can be isolated from human blastocysts or delayed blastocyst stage (as described in WO2006/040763). Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; Gardner et al., [Fertil. Steril. 69: 84, 1998].

It will be appreciated that commercially available stem cells can be also be used with this aspect of the present invention. Human ES cells can be purchased from the NIH human embryonic stem cells registry (<http://escr.nih.gov>). Non-limiting examples of commercially available embryonic stem cell lines are BG01, BG02, BG03, SA01, TE03 (I3), TE04, TE06 (I6), HES-1, HES-2, HES-3, UC01, UC06, WA01, WA07 and WA09 (see also Example 1 of the Examples section which follows).

Stem cells used by the present invention can be also derived from human embryonic germ (EG) cells. Human EG cells are prepared from the primordial germ cells obtained from human fetuses of about 8-11 weeks of gestation using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090, 622.

As mentioned hereinabove, the human stem cells of the present invention may be also derived from a fetal or an adult source, such as for example, mesenchymal stem cells.

The phrase "mesenchymal stem cell" or "MSC" is used interchangeably for fetal or adult cells which are not terminally differentiated, which can divide to yield cells that are either stem cells, or which, irreversibly differentiate to give rise to cells of a mesenchymal cell lineage.

The mesenchymal stem cells of the present invention may be of a syngeneic or allogeneic source.

Mesenchymal stem cells may be isolated from various tissues including, but not limited to, bone marrow, peripheral blood, blood, placenta and adipose tissue. A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301].

Bone marrow can be isolated from the iliac crest of an individual by aspiration. Low-density BM mononuclear cells (BMMNC) may be separated by a FICOL-PAGUE density gradient. In order to obtain mesenchymal stem cells, a cell population comprising the mesenchymal stem cells (e.g. BMMNC) may be cultured in a proliferating medium capable of maintaining and/or expanding the cells. According to one embodiment the populations are plated on polystyrene plastic surfaces (e.g. in a flask) and mesenchymal stem cells are isolated by removing non-adherent cells. Alternatively mesenchymal stem cell may be isolated by FACS using mesenchymal stem cell markers. Examples of mesenchymal stem cell surface markers include but are not limited to CD105+, CD29+, CD44+, CD90+, CD34−, CD45−, CD19−, CD5−, CD20−, CD11B− and FMC7−. Other mesenchymal stem cell markers include but are not limited to tyrosine hydroxylase, nestin and H—NF.

Neural stem cells can also be used in accordance with the present invention. Makers such as Sox1, Sox2, SSEA-1/LeX can be used as possible markers for neural cell selection. Fine separation techniques based on negative FACS assay (in order to exclude lineage-restricted cells) and immunomagnetic beads may be used to obtain purified and homogeneous stem populations (Cai 2003 Blood Cells Mol Dis 31:18-27).

Regardless of their origin, stem cells used in accordance with the present invention are at least 50% purified, more preferably at least 75% purified and even more preferably at least 90% purified. When human embryonic stem cell lines are used, the human ES cell colonies are separated from their feeder layer (x-ray irradiated fibroblast-like cells) such as by mechanical and/or enzymatic means to provide substantially pure stem cell populations.

Once human stem cells are obtained, they may be treated to form aggregates as exemplified in Example 1 of the Examples section.

Cells or preferably aggregates thereof are then subjected to differentiation conditions which comprise retinoic acids, such that neurospheres are allowed to form. The culture medium used is selected according to the stem cell used. Thus, for example, a medium suitable for ES cell growth, can be for example DMEM/F12 (Sigma-Aldrich, St. Lewis, Mo.) or alpha MEM medium (Life Technologies Inc., Rockville, Md., USA), supplemented with supporting enzymes and hormones. These enzymes can be for example insulin (ActRapid; Novo Nordisk, Bagsværd, DENMARK), progesterone and/or Apo transferring (Biological Industries, Beit Haemek, Israel). Other ingredients are listed in Example 1 of the Examples section.

As used herein the phrase "retinoic acid" refers to an active form (synthetic or natural) of vitamin A, capable of inducing neural cell differentiation. Examples of retinoic acid forms which can be used in accordance with the present invention include, but are not limited to, retinoic acid, retinol, retinal, 11-cis-retinal, all-trans retinoic acid, 13-cis retinoic acid and 9-cis-retinoic acid (all available at Sigma-Aldrich, St. Lewis, Mo.).

Retinoic acid is preferably provided at a concentration range of 1-50 µM.

The culture medium may be further supplemented with growth factors which may be present at least in part of the culturing period to promote cell proliferation and facilitate differentiation into the neuronal glial lineages. According to a preferred embodiment of the present invention such growth factors include for example EGF (10-40 ng/ml) and bFGF (10-40 ng/ml) (R&D Systems, Minneapolis, Minn., Biotest, Dreieich, Germany).

As used herein the phrase "neurospheres" refers to quasi-spherical clusters or spheres containing mainly neural stem cells and early multipotent progenitors that can differentiate into neurons, oligodendrocytes and astrocytes as well as other glial cells.

The cells are cultured until ripened neurospheres are formed.

As used herein the phrase "ripened neurospheres" refers to neurospheres in which some of the neural stem cells have differentiated to become specialized oligodendrocyte progenitors having acquired makers of the oligodendrocyte lineage (e.g. Sox10, Nkx2.2, NG2, A2B5), while others have differentiated to become neural progenitors or astrocytes progenitors.

According to a preferred embodiment of this aspect of the present invention the cells are allowed to culture for example for 10-30 (e.g., 20-30) days, at the end of which detached neurospheres are formed. The spheres, or cells dissociated therefrom, are then adhered to substrates and subjected to further expansion with growth factors and eventually to differentiation after removal of growth factors. Examples of adherent substrates which can be used in accordance with the teachings of the present invention include, but are not limited to matrigel or an extracellular matrix component (e.g., collagen, laminin and fibronectin).

Following neuroglial sphere formation (or concomitantly with) or following culture on adherent substrate, the cells are incubated with an agent capable of inhibiting Bone Morphogenetic Protein (BMP) activity.

Bone morphogenetic proteins (BMPs) are signaling molecules, belonging to the TGF-β superfamily, which act locally on target cells to affect cell survival, proliferation, and differentiation, and among other actions, regulate neural cell development.

Figure 1G:
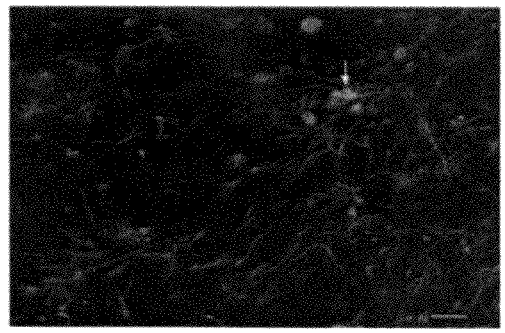
Figure 1H:
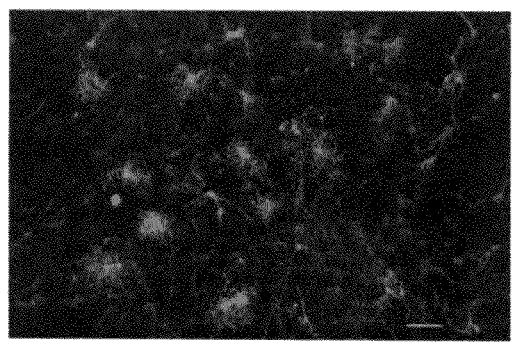

Bone morphogenetic proteins (BMPs), were shown to inhibit oligodendrocyte development from rat fetal brain (Mehler et al., 1997; Mehler et al., 2000). The present inventors have found, as illustrated in FIG. 1 c and Example 1 of the Examples section which follows, that the expression of several members of the BMP family, seen in undifferentiated human ES cells, increased or was even induced after culturing cells with retinoic acid. Expression of some BMPs continued to increase throughout the culturing steps. Since BMPs inhibit oligodendrocyte differentiation, the inhibition of these proteins is critical for inducing differentiation of that lineage.

As used herein the term "agent capable of down-regulating BMP activity" refers to an agent which can at least partially reduce the function (i.e., activity and/or expression) of BMP.

BMP reducing agents include cysteine knot-containing BMP antagonists, which are divided into three subfamilies, based on the size of the cysteine ring; CAN (eight-membered ring), twisted gastrulation (nine-membered ring), and chordin and noggin (10-membered ring). The CAN family is divided further based on a conserved arrangement of additional cysteine residues, and includes gremlin and PRDC; cerberus and coco; DAN; USAG-1 and sclerostin.

Other BMP inhibitors include, but are not limited to, chordin like BMP inhibitor (CHL2), Neuralin (also homologous to chordin) which behave as secreted BMP-binding inhibitors; inhibin (belongs to the TGF-β superfamily); follistatin (which binds to inhibin); GDF3, an inhibitor of its own subfamily (TGF-β), which blocks classic BMP signaling in multiple contexts; Crossveinless-2 (hCV-2), a BMP function inhibitor; Ectodin (available at Qiagene, Valencia, Calif.), which is homologous to sclerostin and inhibits the activity of BMP2, BMP4, BMP6, and BMP7; connective tissue growth factor (CTGF), a BMP receptor antagonist; BMP-3, a BMP receptor antagonist; and gp130 signaling cytokines.

It will be appreciated that oligonucleotide inhibitors, which down-regulate expression of BMP genes (e.g., siRNA) may also be used in accordance with this aspect of the present invention. Methods of genetically modifying stem cells are well known in the art.

In one preferred embodiment of this aspect of the present invention the agent used to inhibit BMP is noggin (e.g., 10-100 ng/ml, e.g., 50 ng/ml used as a Noggin-Fc chimera available from R&D systems, Minneapolis, Minn.). As mentioned, noggin can be used in any culturing step following, and optionally with retinoic acid treatment.

The time and period of treatment with the BMP inhibitor following neurospheres formation affects the differentiation level of the cells. Thus for example, a culturing period starting after the NS cells have been attached to adherent substrates and are cultured with growth factors for 6-15 days and then one day without growth factors produces oligodendrocyte precursors.

A similar culture after 6 days in the absence of growth factors, but in the presence of noggin, produces well differentiated ramified immature oligodendrocytes.

Culturing under the same conditions for 10 days with noggin produces mature oligodendrocytes, expressing MBP.

Instead, addition of noggin early during the ripening of NS increases differentiation to oligodendrocytes albeit in less magnitude than addition at the final culturing stage.

As is further illustrated hereinbelow and in the Examples section which follows, the present invention provides conditions which enable, for the first time, expansion of neurospheres, while retaining their functional phenotype.

Thus, in another embodiment, the present invention provides conditions that enable the expansion of neurospheres for the purpose of, for example, producing glial cells, which retain functional properties. Thus, for example, oligodendrocyte precursors generated according to the teachings of the present invention may be expanded in culture while retaining cell capacity to migrate into affected region in the CNS, and retaining the ability to differentiate into mature oligodendrocytes.

In order to obtain populations of oligodendrocyte precursors that could be passaged and expanded before terminal differentiation, NS are plated on an adherent substrate and thereafter are subjected to one passage by for example, trypsinization to yield dissociated neuroglial sphere cells (huEs-NSc). These, can be further plated on cationic substrates for further culture and passaging, and then be subjected to terminal differentiation.

Examples of adherent substrates which can be used in accordance with the teachings of the present invention include, but are not limited to, cationic substrate which can be poly-D-lysine or Polyornithine with fibronectin (FN).

As shown in the Examples section which follows, cells can be split every 8-10 days for more than 3 passages, preferably more than 5 passages.

As indicated hereinabove, a BMP inhibiting agent can be added at any of the passages, but, as shown in Table 3 and in Example 2 of the Examples section, inventors have found that addition of noggin at the terminal differentiation step (removal of growth factors), yields the highest differentiation into oligodendrocytes.

The present invention further provides methods for producing astrocytes from stem cells cultured in the presence of retinoic acid. This is done by culturing these cells in the presence of growth factors, a BMP inhibitor (as described above), and thereafter removing the growth factors until cells show an astrocytic phenotype (for example, culture with noggin, without growth factors for 5-15 days).

While reducing the present invention to practice, the present inventors have discovered that neurospheres (NS) cultured for 4 days on the adherent matrigel substrate formed a network of neurons, but these tended to disappear after prolonged culture on matrigel. Therefore, when culturing neurospheres for the purpose of producing neurons, inventors have found that culturing and passaging cells on an adherent substance which is not matrigel or the like, does not reduce neuron formation as observed for cells grown on matrigel.

Thus, to generate neurons, ripened NS are preferably plated on a cationic adherent substance and cultured with growth factors. In addition to BMP cultured cells can be passaged for more than 5 times, with the addition of growth factors in every passage.

Sonic Hedgehog (Shh), a factor made in the ventral spinal cord and plays an important role in inducing defined types of neurons as well as oligodendrocyte precursors may be used to promote neuronal cell differentiation. As described in FIG. 6b and in Example 5 in the Examples section inventors have discovered that when Shh was added together with retinoic acid an increase in the density of neuron network was obtained Thus, according to another preferred embodiment of the present invention, Sonic Hedgehog (Shh; R&D Systems, Minneapolis, Minn.) can be added together with RA.

In any of the above protocols laminin and vitamin C may be added to the culture, laminin being an extracellular matrix component which helps cells to adhere, and Vitamin C (ascorbic acid) being a well-known antioxidant.

Populations of cells generated according to the teachings of the present invention may comprise for example at least about 40% of mature oligodendrocytes (comprising at least one mature oligodendrocyte phenotype as described above) and any where between 0-60% cells which comprise a stem cell phenotype. Populations of oligodendrocyte precursors (OPC) may comprise at least 90% of bipolar $O4^+$ cells (and about 10% of cells having a stem cell phenotype).

According to one embodiment of the present invention, the phenotype of any of the neural or glial cells of the populations of the present invention is as close as possible to native cells.

Thus, as illustrated in the Examples section below, the cells differentiated according to the methods of the present invention represent a mature oligodendrocyte like shape, or oligodendrocyte like precursor shape and are accompanied by the presence of the appropriate oligodendrocyte marker.

The percentage of the cells of interest may be raised or lowered according to the intended needs. This may be effected by FACS using an antibody specific for a cell marker. Examples of such markers are described hereinabove. If the cell marker is an internal marker, preferably the FACS analysis comprises antibodies or fragments thereof which may easily penetrate a cell and may easily be washed out of the cell following detection. The FACS process may be repeated a number of times using the same or different markers depending on the degree of enrichment and the cell phenotype required as the end product.

Once differentiated and optionally isolated, the cells may be tested (in culture) for their phenotype. The cultures may be comparatively analyzed for a phenotype of interest (e.g., myelin production, expansion, migration), either in vitro and/or in vivo using biochemical analytical methods such as immunostaining, cell expansion assays (e.g., MTT), migration assays, Western blot and Real-time PCR (some assays are described in Examples 1-5 of the Examples section which follows).

Cells of the present invention may be further cloned and cell-lines of interest may be generated.

Cells generated according to the teachings of the present invention (described hereinabove) and in the Examples section which follows may be used in a myriad of clinical and research applications.

Thus, according to another aspect of the present invention there is provided a method of treating a medical condition of the CNS in a subject-in-need-thereof. The method comprising administering to the subject a therapeutically effective amount of the cells of the present invention (according to the intended use, as further described hereinbelow), thereby treating the medical condition of the CNS.

Subjects treated in accordance with the teachings of the present invention are preferably human subjects.

As used herein, the phrase "medical condition of the CNS" refers to any disorder, disease or condition of the central nervous system which may be treated with the cells of the present invention.

Accordingly, these cells can be used for preparing a medicament (interchangeably referred to as pharmaceutical composition), whereby such a medicament is formulated for treating a medical condition of the CNS.

Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder, an injury, a trauma and a convulsive disorder.

The cells (clones, uncloned cells of s specific type such as oligodendrocytes, or a mixed population of a number of cell types such as oligodendrocytes and astrocytes) used may be selected according to the intended use.

For example, the cells may comprise oligodendrocyte cells and the medical condition can be selected from, for example, the group of autoimmune diseases, multiple sclerosis, Guillan-Barre syndrome or congenital leukodystrophies, adrenoleukodystrophies, Pelizaeus-Merzbacher, Charcot-Marie-Tooth, Krabbe or Alexander disease, vanishing white matter syndrome, progressive multifocal leukoencephalopathy, infectious demyelinating diseases, postinflammatory demyelinated lesions, neurodegenerative diseases, multisystem degeneration, vascular diseases, ischemic white matter damage, vascular leukoencephalopathies, subcortical infarcts, brain trauma, spinal cord trauma, demyelinative injury, neoplasms and oligodendrio-glioma.

In this respect, it should be noted that oligodendrocyte precursor cells (OPCs) may be adventitiously used over mature oligodendrocytes as it is probably the mitotic and migratory capacity of these cells (in contrast to mature cells) which are vital prerequisites for successful remyelination. According to the present invention the remyelinating capacity of the OPCs is significantly enhanced when the OPC have been treated with noggin under the described conditions.

Mature differentiated oligodendrocytes may still be useful as myelinating cells in vivo (Duncan et al. 1992 Dev. Neurosci. 14:114-122). Differentiated and mature human oligodendrocytes may have important applications for testing drugs that can protect oligodendrocytes from toxic or other pathogenic injuries as further described hereinbelow.

Alternatively, the cells may comprise neurons and the medical condition can be selected from, for example, the group of motor neuron diseases, progressive muscular atrophy (PMA), spinal muscular atrophy (SMA), progressive bulbar palsy, pseudobulbar palsy, primary lateral sclerosis, amyotrophic lateral sclerosis (ALS), neurological consequences of AIDS, Alzheimer's disease, developmental disorders, epilepsy, multiple sclerosis, neurogenetic disorders, Parkinson's disease, neurodegenerative disorders, stroke, spinal cord injury and traumatic brain injury.

Yet alternatively, the cells may comprise astrocytes and the medical condition can be selected from, for example, the group consisting of Alexander disease, epilepsy, Alzheimer's disease, spinal cord injury, traumatic brain injury and neurogenesis deficiencies.

As mentioned above, a combination of cells may be used, again depending on the intended need. For example, a combination of oligodendrocytes and astrocytes was indicated adventitious in remyelinating a demyelinated adult rat spinal cord (see Talbott 2005 Exp. Neurol. 11-14).

The cells of the present invention can be administered to the treated subject using a variety of transplantation approaches, the nature of which depends on the site of implantation.

The term or phrase "transplantation", "cell replacement" "cell therapy" or "grafting" are used interchangeably herein and refer to the introduction of the cells of the present invention to target tissue. The cells can be derived from the recipient or from an allogeneic or xenogeneic donor, or from embryonic stem cells.

For example, the cells can be grafted into the central nervous system or into the ventricular cavities or subdurally onto the surface of a host brain or in the spinal cord. Conditions for successful transplantation include: (i) viability of the implant and sufficient number of cells; (ii) retention (e.g., astrocytes) or migration (e.g., OPCs) of the cells within the nervous tissue to the lesions in accordance with the selected population of cells; and (iii) minimum amount of pathological reaction. Methods for transplanting various nerve tissues, for example embryonic brain tissue, into host brains have been described in: "Neural grafting in the mammalian CNS", Bjorklund and Stenevi, eds. (1985); Freed et al., 2001; Olanow et al., 2003). These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation.

Intraparenchymal transplantation can be effected using two approaches: (i) injection of cells into the host brain parenchyma or (ii) preparing a cavity by surgical means to expose the host brain parenchyma and then depositing the graft into the cavity. Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by embedding the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

For transplanting, the cell suspension is drawn up into the syringe and administered to anesthetized transplantation recipients. Multiple injections may be made using this procedure.

The cellular suspension procedure thus permits grafting of the cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20, 1976), by removing bone overlying the brain and stopping bleeding with a material such as a gelfoam. Suction may be used to create the cavity. The graft is then placed in the cavity. More than one transplant may be placed in the same cavity using injection of cells or solid tissue implants. Preferably, the site of implantation is dictated by the CNS disorder being treated.

For example, in treating multiple sclerosis transplantation into a small number of carefully chosen lesions, for example, the optic nerves, the spinal cord, or the superior cerebellar peduncle can be effected.

In other inherited disorders of myelin metabolism, a systemic mode of administration may be used to exploit the migratory capacity of OPCs and both the circulation of the brain and the blood. In these cases disruption of the blood-brain barrier and/or supplementation with growth factor infusion or growth/trophic factor secreting cells.

Since non-autologous cells are likely to induce an immune reaction when administered to the body, several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxy-ethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Human ES cells that are "patient specific" and therefore would not be subject to immune reaction may be obtained by nuclear transfer in enucleated oocytes (so called therapeutic cloning). Alternatively, human ES cell banks may be used to find cells that are HLA matched to the patient. In addition, genetic engineering of the ES cells may be done to down-regulate histocompatibility antigens and reduce the risk of immune reaction. For this purpose, it is possible to use siRNA or some viral genes (Lee E M, Kim J Y, Cho B R et al, Biochem. Biophys. Res Commun. 326, 825-835, 2005).

In any of the methods described herein, the cells can be administered either per se or, preferably as a part of a pharmaceutical composition that further comprises a pharmaceutically acceptable carrier.

As used herein a "pharmaceutical composition" refers to a preparation of one or more of the chemical conjugates described herein, with other chemical components such as pharmaceutically suitable carriers and excipients. The purpose of a pharmaceutical composition is to facilitate administration of a compound to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the present invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the tissue or organ of interest. Thus, for example the cells may be administered directly into a specific region of the brain or to the spinal cord.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, animal models of demyelinating diseases include shiverer (shi/shi, MBP deleted) mouse, MD rats (PLP deficiency), Jimpy mouse (PLP mutation), dog shaking pup (PLP mutation), twitcher mouse (galactosylceramidase defect, as in human Krabbe disease), trembler mouse (PMP-22 deficiency). Virus induced demyelination model comprise use if Theiler's virus and mouse hepatitis virus. Autoimmune EAE is a possible model for multiple sclerosis.

Animal models for neuronal diseases include 6-OHDA-lesioned mice which may be used as animal models of Parkinson's. In addition, a sunflower test may be used to test improvement in delicate motor function by challenging the animals to open sunflowers seeds during a particular time period.

Transgenic mice may be used as a model for Huntingdon's disease which comprise increased numbers of CAG repeats have intranuclear inclusions of huntingtin and ubiquitin in neurons of the striatum and cerebral cortex but not in the brain stem, thalamus, or spinal cord, matching closely the sites of neuronal cell loss in the disease.

Transgenic mice may be used as a model for ALS disease which comprise SOD-1 mutations.

The septohippocampal pathway, transected unilaterally by cutting the fimbria, mimics the cholinergic deficit of the septohippocampal pathway loss in Alzheimers disease. Accordingly animal models comprising this lesion may be used to test the cells of the present invention for treating Alzheimers.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated Parkinson's patient will be administered with an amount of cells which is sufficient to alleviate the symptoms of the disease, based on the monitoring indications.

The cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA. Additionally, the cells of the present invention may be co-administered with other cells.

Following transplantation, the cells of the present invention preferably survive in the diseased area for a period of time (e.g. at least 6 months), such that a therapeutic effect is observed. As described in Example 4, the cells of the present invention were shown to migrate myelinate in shiverer mouse brain.

Generally, any method known in the art can be used to monitor success of transplantation. For example, MRI can be used for visualizing brain white matter and studying the burden of delyelinating lesions as currently practiced for monitoring MS patients. Magnetization transfer contrast can be used to monitor remyelination (Deloire-Grassin 2000 J. Neurol. Sci. 178:10-16). Magnetic resonance spectroscopy measurement of N-acetyl-aspartate levels can be used to assess impact on local neuron/axon survival. Using paramagnetic particles to label cells before transplantation enabling their dispersion to be tracked by MRI. Serial neurophysiology is useful for monitoring conduction. The optic nerve has particular advantages in this respect.

Other approaches to more generalized neurophysiological assessment are described in Leocani et al. Neurol Sci. 2000; 21(4 Suppl 2):S889-91 which may be useful for interventions aimed at multifocal or more diffuse myelin repair. Notwithstanding, it is appreciated that clinical improvement may also be assessed. Demyelination causes alterations of stature (trembling, shivering) and locomotion. Children with leukodystrophies have motor and intellectual retardation. Electrophysiological measures of sensory and motor nerve conductivity, for example H-wave, are classical method used in monitoring neuropathies linked to demyelinating peripheral lesions (Lazzarini et al, eds (2004) Myelin biology and disorders, Elsevier Academic Press, San Diego, Calif.).

As mentioned above, cells of the present invention can be used as an imperative tool for in vitro screening of drugs.

Thus, according to yet another aspect of the present invention there is provided a method of determining an effect of a treatment on neural cell functionality, the method comprising subjecting a cell of the present invention (e.g., oligodendrocyte) to the treatment (e.g., drug, condition such as electrical treatment and an irradiation treatment); and determining at least one of a structural or functional phenotype of the treated cell as compared to an untreated cell, thereby determining an effect of the treatment on neural cell functionality.

Qualifying the effect of a treatment of interest on the cells of the present invention can be used to identify and optimize treatments capable of restoring the neural function, and hence can be used to identify and optimize drugs suitable for treating neural disorders (e.g., including treatment methods envisaged by the present invention).

Furthermore, qualifying the effect of a treatment (either directed to diseases of the CNS or any other tissue) on neural functionality can be used to assess the toxicity of such clinical treatments.

Thus, this aspect of the present invention can be preferably utilized to determine the therapeutic and toxic effects of various treatments, such as drug treatments, and electrical treatments, on neural function.

Hence the method of the present invention can be used to screen and/or test drugs.

This aspect of the present invention can be also utilized to obtain gene expression profiles and changes thereof in cells of the present invention subjected to a treatment. Thus, the method according to this aspect of the present invention can be used to determine, for example, gene expression pattern changes in response to a treatment.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Conversion of Human ES Cells into Cells Expressing Genes Characteristic of the Oligodendrocyte Lineage ES cells were cultured with a combination of retinoic acid (RA) treatment followed later by the addition of Noggin addition to produce mature oligodendrocytes, defined by the expression of myelin proteins.

Materials and Experimental Procedures
Culturing Media—
ES1: ESC Growth Medium

The growth medium (ES1) consisted of DMEM/F12 (Sigma-Aldrich, St. Lewis, Mo.) supplemented with 20% knockout serum replacement (KSR, Gibco BRL/Invitrogen, Gaithersburg Md.), MEM nonessential amino acids (1/100; Gibco BRL/Invitrogen, Gaithersburg Md.), 100 µM beta-mercaptoethanol (Gibco BRL/Invitrogen, Gaithersburg Md.), 1 mM Na pyruvate, 2 µg/ml heparin and with 6 to 8 ng/ml human recombinant basic fibroblast growth factor (bFGF, Cytolab, Rehovot, Israel).

ITTSPP/B27 Medium

The medium was composed of 50% (v/v) of DMEM/F12 (Sigma-Aldrich, St. Lewis, Mo.) containing 2% B27 supplement (Gibco BRL/Invitrogen, Gaithersburg Md.) and 50%

(v/v) of DMEM/F12 containing 25 µg/ml insulin (ActRapid; Novo Nordisk, Bagsværd, DENMARK), 50 µg/ml human Apo transferrin (Biological Industries, Beit Haemek, Israel), 6.3 ng/ml progesterone (Sigma P01304), 10 µg/ml putrescine (Sigma-Aldrich, St. Lewis, Mo.), 50 µg/ml sodium selenite (Sigma), and 40 ng/ml triiodothyronin (T3, Sigma), with penicillin (100 U/ml) and streptomycin (100 µg/ml).

T-Medium

50% (v/v) ES1 medium, and 50% (v/v) of ITTSPP/B27 medium.

N2/B27 Medium

The medium was composed of DMEM/F12, 0.5% (v/v) N2 supplement (Gibco BRL/Invitrogen, Gaithersburg Md.), 1% (v/v) B27 supplement, 10 ng/ml of EGF, and 10 ng/ml of bFGF Human ESC Line Culturing Human embryonic stem cell lines (huESC; for example, I-3 or I-6 as in Amit and Itskovitz-Eldor, 2002), were cultured (in ES1), frozen and thawed, as previously described (Amit et al., 2004), on feeder layers of mouse embryonic fibroblasts (MEF) which have been gamma-irradiated at 37° C., in a 5% $CO_2$ incubator. About 4 days following seeding, huES cells colonies were washed with DMEM/F12, and detached by collagenase IV (Worthington Biochemical Corp. Lakewood, N.J.), freshly prepared, 1.2 mg/ml in DMEM/F12, using 1 ml per well for 45 to 90 minutes in the incubator. The detached aggregates were thereafter cultured as described above or subjected to the differentiation protocol as described hereinbelow and outlined in Table 1.

Differentiation of ES Cells into Oligodendrocytes

The following steps were taken for initiating ES cell differentiation:

1. Step T: Transition Step

Collagenase detached huESC colonies pooled from six 6-well plates, into a 15 ml tube supplemented with ES1 medium, were let to sediment by gravity for about 30 minutes in the incubator (37° C.). Colonies were then washed once in ES1 medium and then transferred to 12×6 cm tissue culture plates in 5 ml transition medium (T-medium) consisting of 50% (v/v) ES1 medium, and 50% (v/v) of ITTSPP/B27 medium. Growth factors (GF), recombinant human EGF (20 ng/ml, R&D Systems, Minneapolis, Minn.) and recombinant human bFGF (4 ng/ml, Biotest, Dreieich, Germany) were added to the transition medium. Thereafter (1d), some cells adhered but the bulk of huESC colonies and aggregates remained in suspension and were transferred to 12 bacterial (non-adherent) plates in the same transition medium and cultured for 1 day. Then, 10 µM retinoic acid (RA, Sigma-Aldrich, St. Lewis, Mo.) was added to the T-medium and cells were cultured for an additional day.

2. Step R: Retinoic Acid Treatment

The medium was switched to ITTSPP/B27 containing 20 ng/ml of EGF and 10 µM RA. Medium was changed every day for 7 days, and colonies were concentrated by gravity, without centrifugation.

3. Step S: Suspension Culture

During this step, which allows for ripening of neurospheres (NS), the aggregates were cultured in ITTSPP/B27 medium supplemented with 20 ng/ml EGF, for 18 days, changing medium every two days. The ITTSPP/B27 medium was, or was not supplemented with 50 ng/ml Noggin-Fc chimera (R&D systems, Minneapolis, Minn.), in order to examine the effect of noggin. The addition of bFGF 20 ng/ml at this step was not found to be helpful.

4. Steps M1,2: Adherence to Matrigel-Coated Plates

Spheres or aggregates from one original 6-well plate were distributed to another 6-well plate which had been coated for 1.5 hours at room temperature with matrigel (Matrigel low growth factor concentration; BD Biosciences, Clontech, Palo Alto, Calif., diluted 1:30 in DMEM/F12 Pen-Strep). After one day, the unbound aggregates were discarded and fresh ITTSPP/B27 medium, supplemented with 20 ng/ml EGF, was added. Medium was changed every 3-4 days.

5. Passage with Trypsin

Following 1-2 weeks, aggregates were detached and partially dissociated by a short treatment with trypsin 0.05% (2-3 min, 37° C.; Biological industries, Beit Haemek, Israel, diluted in PBS, —Ca and —Mg). Trypsin was rapidly neutralized by addition of 4 volumes of BSA (2 mg/ml; Sigma for Tissue culture) in ITTSPP/B27, and centrifugation at (200 rpm, 10 min), followed by another wash with BSA. This treatment dissociates the aggregates to small clusters that are seeded again onto matrigel-coated plates (at dilution 1:3), in ITTSPP/B27, 20 ng/ml EGF, for another 1-2 weeks (step M2).

6. Steps F1,2: Terminal Differentiation on Matrigel

In step F1 (3 days), the medium was changed to ITTSPP/1327 containing EGF 5 ng/ml and bFGF 5 ng/ml, together with mouse laminin 1 µg/ml, and Vit C (50 µg/ml; Sigma-Aldrich, St. Lewis, Mo.). Some of the wells were treated with noggin (50 ng/ml Noggin-Fc chimera; R&D systems, Minneapolis, Minn.), 2 days after seeding, and noggin was continued thereafter. In step F2, cells were cultured 6 or 10 days in the same medium without growth factor, but with or without noggin. The medium was changed every two to four days.

The procedures and different conditions used for deriving oligodendrocytes from human ES cells described above are summarized in Table 1 below, several culturing conditions (e.g., addition of steps, or time duration of steps) were administered to the cells (numbered 1-4 in Table 1). Conditions 2-4 are further explained in Example 2-5.

TABLE 1

| Step: | Conditions (conc.): | 1 | 2 | 3 | 4 |
|---|---|---|---|---|---|
| T | EGF (20)#, bFGF (4) in ES1/[ITTSPP/B27] | | | 2 d | |
| R | Retinoic acid 10 µM + EGF (20), [ITSPP/B27] | | | 7 d | |
| S | EGF (20) in [ITSPP/B27] | 18 d ±noggin | 18 d ±noggin | 18 d | 18 d |
| M1 (matrigel) | EGF (20) in [ITSPP/B27] | 9 d | 17 d | 13 d | 13 d |
| M2 (matrigel) | Trypsin passage (P1) and replate in same | — | 11 d | 21 d | 21 d |

TABLE 1-continued

| Step: | Conditions (conc.): | 1 | 2 | 3 | 4 |
|---|---|---|---|---|---|
| D1 (dissociated cells) | Trypsin (P2) and replate in EGF (20) in [ITSPP/B27] | — | Trypsin dissociation of the cells Polyornithine FN, laminin 3 d | Poly D-Lysine 1 d | Poly D-Lysine 1 d |
| D2 (dissoc. cells) | EGF (10) + bFGF (10) in [N2/B27] | — | 8 d ±noggin | 15 d | 15 d |
| D3 (dissoc. cells) | Passage (P3, Hanks) and replate in same | — | — | 6 d ±noggin | 13 d ±noggin |
| D4 (dissoc. cells) | Passage (P4, Hanks) and replate in same | — | — | — | 8 d ±noggin |
| F1 | EGF (5) + bFGF (5) in [N2/B27] | 3 d* ±noggin | 3 d ±noggin | — | — |
| F2 | No GF in [N2/B27] | 6 or 10 d* ±noggin | 6 d ±noggin | 6 or 10 d ±noggin | 6 d ±noggin |

*differentiation step F while still on matrigel and in ITSPP/B27 medium
concentrations in ng/ml.

RT-PCR total RNA was isolated from cultures at different culture steps using Tri-Reagent (Molecular Research Center, Cincinnati, Ohio) and RT-PCR was carried out by standard technology as previously described (Slutsky et al., 2003).

Expression was checked for the following genes, as described in table 2 below, including the expression of the control gene G3PDH. Also provided in the table are primer sequences used for each gene. For G3PDH, primers from Clontech (Palo Alto Calif., catalog #9805-1) were used.

TABLE 2

| Human Gene | Sequence | Nucleotide number | Accession number | SEQ ID NO. |
|---|---|---|---|---|
| BMP-7 F | CCTTCATGGTGGCTTTCTTC | 946-965 | NM_001719 | 1 |
| BMP-7 R | CCAAAGGGTCTGAATTCTCG | 1444-1425 | | 2 |
| BMP-2 F | AGAACTACCAGAAACGAGTGGG | 1142-1163 | NM_001200 | 3 |
| BMP-2 R | CGCTGTTTGTGTTTGGCTTG | 1651-1632 | | 4 |
| BMP-6 F | CGGTTCTTTACTTTGATGAC | 1639-1658 | NM_001718 | 5 |
| BMP-6 R | GATAGACAGTACTGAACCAGC | 2142-2122 | | 6 |
| BMP-4 F | CATTTATGAGGTTATGAAGCC | 1014-1033 | NM_001202 | 7 |
| BMP-4 R | CCACCTTATCATACTCATCCAG | 1654-1633 | | 8 |
| BMP-11 F | GCGACTAAAACCCCTAACTG | 632-651 | AF100907 | 9 |
| BMP-11 R | CTGCACCAAATGGGTATGC | 1118-1099 | | 10 |
| Nkx2.2 F | TGCCTCTCCTTCTGAACCTTGG | 1388-1409 | NM_002509 | 11 |
| Nkx2.2 R | GCGAAATCTGCCACCAGTTG | 1724-2705 | | 12 |
| OCT3-4 F | CTTGCTGCAGAAGTGGGTGGAGGAA | 662-686 | NM_002701 | 13 |
| OCT3-4 R | CTGCAGTGTGGGTTTCGGGCA | 830-810 | | 14 |
| olig1 F | TTGCATCCAGTGTTCCCGATTTAC | 1688-1711 | NM_138983 | 15 |
| olig1 R | TGCCAGTTAAATTCGGCTACTACC | 2077-2054 | | 16 |
| olig2 F | AAGGAGGCAGTGGCTTCAAGTC | 368-388 | NM_005806 | 17 |
| olig2 R | CGCTCACCAGTCGCTTCATC | 681-662 | | 18 |
| PDGFR F | CTATCCACACTGTCAAACAGGTTG | 5299-5322 | NM_006206 | 19 |
| PDGFR R | TCTGCTGGACTGAGAAGTTTCATC | 5751-5729 | | 20 |
| PLP F | CTGCTCACCTTCATGATTGC | 825-844 | NM_000533 | 21 |
| PLP R | TGACTTGCAGTTGGGAAGTC | 1149-1168 | | 22 |
| REX-1F | TGAAAGCCCACATCCTAACG | 1283-1302 | NM_174900 | 23 |
| REX-1R | CAAGCTATCCTCCTGCTTTGG | 1839-1819 | | 24 |
| SOX 10 F | GCCTGTTCTCCTGGGGCTTTGCTGC | 1889-1865 | NM_006941 | 25 |
| SOX 10 R | CATCCACCTCACAGATCGCCTACAC | 1396-1420 | | 26 |
| TGFβ1 F | CAGCAACAATTCCTGGCGATAC | 1389-1410 | NM_000660 | 27 |
| TGFβ1 R | GGACAGCTGCTCCACCTTG | 2007-1989 | | 28 |

Results

In order to examine gene expression during the different culture steps, and the effect of noggin on this expression, RT-PCR was effected for genes expressed during ES maturation to oligodendrocytes, in the different culture steps, with or without the addition of noggin. FIG. 1a shows the expression of genes for the transcription factors Nkx2.2, Sox10 and Olig2 believed to be characteristic of the oligodendrocyte lineage (Gokhan et al., 2005). Whereas Olig1 and Olig2 were expressed after step R (FIG. 1a, lane 1; retinoic acid treatment), the expression of the two other genes was seen only when noggin was added, after step S (Suspension of culture, where neurospheres are allowed to ripen; FIG. 1a, lane 3). Sox10 was not seen after step S without noggin (FIG. 1a, lane 2). FIG. 1b shows that using a protocol which was successful for differentiation of murine ES cells into oligodendrocytes (Zhang et al., 2004; Zhang et al., 2006), based on bFGF treatment but with neither RA nor noggin, failed to induce Nkx2.2 in human ES cells, while Sox10 (and Olig2, not shown) were expressed. The same was observed when 40 ng/ml triiodothyonine was added (FIG. 1b, right lane). In addition, expression of growth factor receptor PDGF-Rα, characteristic of early precursors of the human oligodendrocyte lineage (Zhang et al., 2000) was high following RA treatment (FIG. 1a, lane 1) and decreased as expected later (FIG. 1a, lane 2) and more so if noggin was added (FIG. 1a, lane 3). This is an indication that noggin acts on differentiation of OP cells. The myelin proteolipid protein (PLP) is seen increasing, whereas markers of undifferentiated pluripotent stem cells, such as Oct4 and Rex1, are down-regulated after step S with noggin (lane 3). The rationale for adding noggin to cultures treated with retinoic acid is illustrated by FIG. 1c. Noggin is an inhibitor counteracting the effect of Bone morphogenetic proteins (BMPs), which were shown to inhibit oligodendrocyte development from rat fetal brain (Mehler et al., 1997; Mehler et al., 2000). FIG. 1 c shows that the expression of several members of the BMP family, seen sometimes in undifferentiated human ES cells (lane 1), is increased or even induced after step R (FIG. 1c, lane 2). Expression of some BMPs, such as BMP-6 and 7, continues to increase at step S, M and F (lanes 4, 5, 6). These BMPs are likely to be the targets of noggin's effect.

Example 2

Effect of Noggin on the Terminal Differentiation of Human Oligodendrocytes Derived from ES Cells Effect of noggin on human oligodendrocyte differentiation was examined by direct visualization and counting of immunostained cells cultured with and without noggin.

Materials and Experimental Procedures
Culture and Culture Conditions
culture conditions were effected as described in Example 1.

Immunostaining
Cells were fixed in 12 or 24-well tissue culture plastic plates with 4% paraformaldehyde (PFA), washed with PBS, and kept at 4° C. before staining. Non-specific staining was blocked with normal goat serum (5% w/v in PBS) for 30 min at RT. Thereafter primary mouse monoclonal (mMc) antibodies, diluted in 1% goat serum, were administered. Antibodies used were: anti PDGFR (mMc IgG1, Santa Cruz, 1:500), O4 (mMc IgM, R&D Systems, 1:1000), O1 (mMc IgM, received from Dr Sheila Harroch, Pasteur Institute, Paris), anti tubulin-βIII (mMc IgG1, Cowance, 1:1000), and antibody 1281 (human nuclei antigen HNA, Chemicon). Following overnight exposure to the appropriate antibody (4° C.), biotinylated goat anti-mouse IgG1 (Southern Biotech, 1:50) was added for 30 minutes, followed by Cy3-tagged streptavidine (ABC laboratories, 1:2000). For double staining, O4 or O1 was revealed with anti mIgM-FITC (Chemicon, 1:75, 1 hour) and cells fixed again with 3% PFA for 10 minutes, permeabilized by 0.2% Triton-X100 for 10 min when necessary, and reacted with the other antibody. Staining for MBP was with rat monoclonal anti MBP (ab7349, AbCam, 1/500), and Cy3-conjugated Affipure goat anti rat IgG (Jackson laboratories, 1:500). Staining for GFAP was with Cy3-conjugated mMc anti-GFAP (Sigma-Aldrich, St. Lewis, Mo.; 1:1000). Staining was effected for 1 hour at RT, followed by the nuclear fluorescent dye DAPI (Sigma-Aldrich, St. Lewis, Mo., 0.05 μg/ml). All coverslips were mounted in Mowiol (Calbiochem, LaJolla, Calif.). An Olympus IX-70 FLA microscope with a DVC-1310C digital camera (DVC, Austin, Tex.) was used and images were processed with Photoshop and analyzed with Image-ProPlus software (Media Cybernetics, Silver Spring, Md.), in order to measure Integrated Optic Density (IOD) of color-specific pixels and MBP fiber length. Statistical analyses was with two-tailed Student t-test and Anova, using Instat (GraphPad Software Inc.) or JMP 5.0 software (SAS Institute, Cary, N.C.)

Cell Count

The number of O4$^+$ cells with oligodendrocyte branching morphology was counted in fields of 0.4 mm$^2$. Cells were counted following the differentiation step, with cells on matrigel, as in Table 1, condition 1, described in Example 1. Additionally, dissociated neurosphere cells plated on poly-D-lysine (PDL) for expansion and differentiation, as described in Table 1, conditions 2, 3, 4 respectively, were counted. In all cases, cells were fixed after 6 days of differentiation without growth factors. p-value was obtained by two-tailed Student's t-test.

Results
Immunostaining

In order to follow cell development under the administered culture conditions, immunostaining was done with antibodies to neuron-specific tubulin-βIII to follow the creation of neurons, and with antibodies against oligodendrocyte-specific marker O4$^+$, the astrocyte marker GFAP and the oligodendrocyte precursor marker PDGFR, to follow glial cell types and the developmental stage of the cells. Results show that after 4 days on matrigel (step M, as described in Example 1) the outgrowth from the neurospheres contains a network of neural processes and a few round cells labeled by the O4$^+$ marker (FIG. 1 d). After 8 days in step M, the O4$^+$ cells are still of small round, monopolar morphology (FIG. 1 e, panel 1 and 3) and are also stained for the astrocyte marker GFAP (FIG. 1 e, panel 2). Much less neurons survived at this stage (not shown). Upon removal of EGF and addition of noggin for 6 days (still on matrigel, as seen in FIG. 1 f), the O4$^+$ cells develop into elongated bipolar cells, staining positive for the PDGF-receptor, which is a marker of oligodendrocyte precursors. Notably, a number of O4$^+$ cells have already undergone terminal differentiation to highly branched oligodendrocytes, and in accordance have down-regulated the PDGF-receptor. After 10 days without growth factors, a strong effect of noggin on the number of well-developed oligodendrocytes displaying ramified branches, is evident (FIGS. 1 g-h). Without noggin (FIG. 1 g), most O4$^+$ cells are still elongated bipolars, whereas with noggin (FIG. 1 h) many O4$^+$ cells with the typical oligodendrocyte morphology are seen. Table 3 given below shows quantitative results of such experiments showing that the addition of noggin at step F1,2 (terminal differentiation steps, as described in Table 1, conditions 1) produces the highest increase in oligodendrocytes per field. Addition of noggin at step S (ripening of neurospheres) also increase oligodendrocyte number albeit less than addition at the terminal step F.

TABLE 3

| | Number of oligodendrocytes per field | | | |
|---|---|---|---|---|
| Conditions | Without Noggin | With Noggin | Fold | p-value |
| A. On Matrigel Add noggin at: | | | | |
| Step F | 0.66 ± 0.6 (N = 15) | 5.76 ± 4.2 (N = 25) | 8.7 | 0.0001 |
| Step S | | 1.50 ± 1.4 (N = 14) | 2.2 | 0.043 |
| Steps F and S | | 2.95 ± 1.7 (N = 20) | 4.4 | 0.0002 |
| B. Dissociated cells | | | | |
| Passage 2 | 0.57 ± 0.5 (N = 7) | 5.20 ± 1.7 (N = 10) | 9.1 | 0.0001 |
| Passage 3 | 1.43 ± 3.1 (N = 16) | 10.14 ± 5.2 (N = 7) | 7.1 | 0.0001 |
| Passage 4 | 2.00 ± 1.4 (N = 9) | 12.05 ± 3.6 (N = 6) | 6.0 | 0.0001 |

Figure 2A:
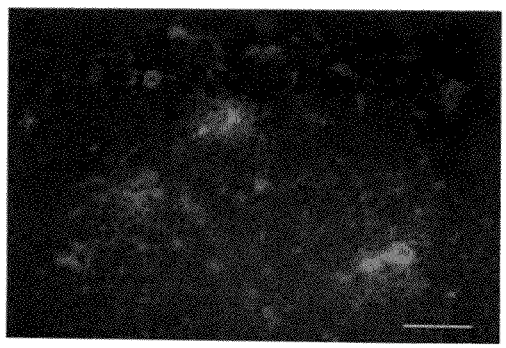
FIGS. 2 *a-g* depict mature myelin basic protein (MBP)-positive oligodendrocytes differentiated from the human ES cells following culture conditions as described in Table 1, condition 1, in Example 1 in the Examples section.
Figure 2B:
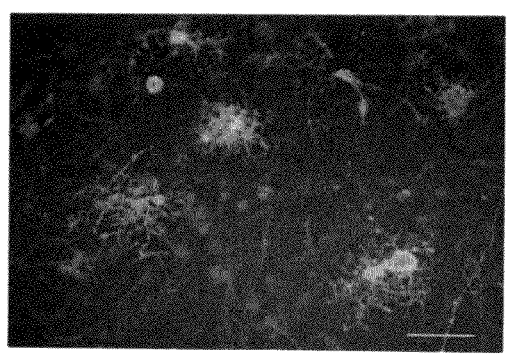

O4 is a marker of immature oligodendrocytes, but staining for the MBP protein (FIG. 2a) shows that many of the O4$^+$ cells (FIG. 2b) express this myelin component indicating that they are maturating oligodendrocytes. Some cells are double positive (see also FIG. 2c), some are still only O4$^+$ (FIG. 2d) and some have matured to the stage where O4 has ceased to be expressed in the MBP-positive oligodendrocytes (FIG. 2e). The number of MBP-expressing cells is high after addition of noggin (FIG. 2f), and quantitation of the effect of noggin (FIG. 2g) shows a very significant stimulation of the number of MBP$^+$ oligodendrocytes Example 3

Dissociated Neuroglial Sphere Cells (NSc) Differentiating into Mature Oligodendrocytes Materials and Experimental Procedures
Culture and Culture Conditions
culture conditions were effected as described in Example 1.
Cell Expansion
In order to obtain populations of oligodendrocyte precursors that could be passaged and expanded before terminal differentiation, the clusters, aggregates or spheres on matrigel were subjected to one passage by mild trypsinization (as described in Example 1) while still on matrigel (passage 1), and then detached from matrigel and dissociated by trypsin to yield dissociated cells. These human ES cell-derived dissociated neuroglial sphere cells (huEs-NSc), were plated onto cationic substrates for further culture (passage 2), and then terminal differentiation according to the following steps, as outlined in Table 1, conditions 2-4, in Example 1.
Step D1: Dissociated Cells Plated on Cationic Substrates
Tissue culture plates were coated with bovine plasma fibronectin (250 µg/ml FN, Sigma-Aldrich, St. Lewis, Mo.) diluted in PBS (plus Ca and Mg) transferred from well to well, dried and coated with poly-L-ornithine (PO, Sigma-Aldrich, St. Lewis, Mo.) and washed three times with water. Alternatively, tissue culture plates were coated with Poly-D-Lysine (20 µg/ml PDL, Sigma-Aldrich, St. Lewis, Mo.), in 10 mM borate buffer, for 2 hours to overnight at 37° C., and washed three times with sterile water. The huES-NS cells or small aggregates, detached from matrigel and dissociated by trypsin, were seeded on PDL or FN—PO coated plates in ITTSPP/B27 supplemented with EGF 20 ng/ml for one day.
Steps D2-4: Expansion of Dissociated huES-NSc
One day after culturing with ITTSPP/B27 supplemented with EGF 20 ng/ml, the medium was changed to N2B27 medium, and mouse laminin (1 µg/ml, Sigma-Aldrich, St. Lewis, Mo.) was added to the medium during the first seeding. Cells were split every 8 to 10 days.
For passage 3 to passage 5, the cells from PDL plates were dissociated in Hank's balanced salt solution (HBSS; Invitrogen/Gibco, Gaithersburg Md.) without Ca and Mg. Cells were first quickly washed with warm HBSS, and immediately added with 0.4 ml of HBSS per well, while being scraped gently with a rubber policeman. The cells were then centrifuged, dissociated by up and down pipetting, and reseeded (at 1:2 dilution) onto PDL-coated plates in N2B27 with laminin. Cells split with HBSS have a tendency to form rosette-type aggregates. When aggregates were more than 0.5 mm diameter, and could not be dissociated with HBSS, 0.025% trypsin-EDTA, was added for exactly 2 min, and neutralization with BSA. Surviving cells formed monolayers and very small aggregates, and were usually split 1:3. In order to define the effect of noggin on cell development, 50 ng/ml noggin was added at these steps, as indicated in Table 1, Example 1.
Step F2: Terminal Differentiation of Dissociated Cells
At the different passages, terminal differentiation was induced by removing the growth factors for 6-10 days. Step F1 (as described in Example 1) could be omitted (see Table 1 conditions 3, 4). Whenever growth factors were removed, 1 µg/ml mouse laminin, and 50 µg/m Vit C were added to the N2/B27 medium. Noggin, 50 ng/ml, was continued as indicated in Table 1.
O1 Staining
staining with O1 antibodies specific for mature oligodendrocytes was effected as previously described (Zhang et al, 2004).
Results
Effect of Noggin on Oligodendrocyte Development
in order to assess the effect of noggin addition to oligodendrocyte development, the number of oligodendrocytes was compared in fields examined from cells cultured with and without noggin addition, at different culture steps, as described in Examples 1 and 2 and in Table 1. Addition of noggin was found to increase the number of O4$^+$ cells with oligodendrocyte morphology (multiple ramified branches) by 9-fold, as presented in Table 3, B, Passage 2). At this passage, the total O4$^+$ cells represented about 15% of the total cells, and those with ramified oligodendrocyte shape were about 5% of the total cells. Results also confirm that addition of noggin at the early step S, resulted in a much lower fold increase of oligodendrocytes formed in the differentiation step (only 1.77±1.2 versus 5.20±1.7, shown for passage 2 in table 3; p<0.0001). The use of bFGF alternating with EGF during step S (without noggin) was deleterious and only 0.66±0.5 oligodendrocytes formed in the final differentiation step F with noggin, a much lower value than 5.20±1.7 which was obtained if EGF alone was used in step S (see Table 3B). While this early exposure to bFGF impaired oligodendrocyte development, it was nevertheless found that the combination of bFGF and EGF was better than EGF alone for the expansion of dissociated precursor cells at step D2. Hence, the timing of factor addition was found to be very critical in this procedure. In addition, purity and differentiation capacity of oligodendrocytes increased after multiple passages. The sub-passaged culture (fixed within a day after passage 4) showed a rather homogeneous population of O4$^+$ bipolar cells (as shown in FIG. 3a). Indeed, less than 10% of the nuclei belonged to O4 negative cells. The bipolar cells could be differentiated (10 days without GF, but with noggin) to form dense fields of highly branched O4$^+$ oligodendrocytes (FIG. 3b). Differentiated cells exhibited the complex branching pattern and the formation of flat membranes, typical of maturating oligodendrocytes, as clearly seen in FIG. 3c To further assess Development of mature oligodendrocytes, staining with O1 antibodies specific for mature oligodendrocytes was effected, as described previously (Schachner et al., 1981). O1 staining was found to be high in the cell bodies and in the branches (FIG. 3 d). Astrocytes, stained for GFAP were observed as well (FIG. 3 d).

A higher number of oligodendrocytes per field, formed after terminal differentiation, was found at passages 3 and 4 than at earlier steps (Table 2, B). The stimulating effect of noggin addition during steps D and F was clearly seen in all cases (Table 2,B). Although more oligodendrocytes formed in the control cultures at the higher passages, the proportion of oligodendrocytes became higher after these sub-passages and reached 43% of the total cells in the culture.

Taken together, these results show that the capacity of the huESC-derived precursors (OP) to differentiate into oligodendrocytes is not only conserved through several passages but actually increases, further substantiating the ability of the present invention to makes large scale expansion of oligodendrocytes possible.

Example 4

The Effect of Noggin on the Myelination Capacity of Human Oligodendrocyte Precursor Cells In Vivo Myelination capacity of human oligodendrocyte precursor cells as effected by noggin was determined in vivo in shi$^{-/-}$ Shiverer mice, which lack MBP immunoreactivity in the CNS Reagents and Experimental Procedures
Animal Model
Shiverer mice have an extensive deletion in the MBP gene (Roach et al., 1985) and in a homozygous shi-/- animal there is no MBP immunoreactivity in the CNS. The appearance of fibers showing immunostaining for MBP following transplantation of oligodendrocyte precursors therefore indicates, that the transplanted cells have the capacity to myelinate endogenous neurons (Lachapelle et al., 1983).

Transplantation of huES-NSc in Shiverer Mice
For transplantation, ES cell-derived dissociated neuroglial sphere cells (huEs-NSc) were prepared as described in Example 3. The culture steps from step T to step D3 that were followed, are outlined in Table 1 condition 3. in Example 1. However, Step D3 was for 9 days, with and without 50 ng/ml noggin. Growth factors were then removed for one day, during which 1 µg/ml laminin, and 50 µg/m Vit C were added to the N2/B27 medium (step F2, as described in Example 1). The culture was thereafter subjected to the short trypsin treatment (see Example 1) and the cells were injected intraventricularly to homozygous shiverer mice. One day old shi/shi pups were anesthetized by brief hypothermia and received an injection of $10^5$ cells in 2 µA over a period of 3 minutes, into the brain third ventricule, using a Hamilton 10 µl syringe. The pups were then warmed and returned to their mothers. Four weeks following transplantation, the animals were given a pentobarbital anesthesia and killed by aortic perfusion with 4% PFA in 0.1 M phosphate buffer, pH 7.4. The brains were cryoprotected in phosphate-buffered 30% sucrose overnight. Serial 20 µm-thick coronal cryostat sections were prepared from each brain and were mounted on superfrost plus slides (Erie Scientific, Portsmouth, N.H.). Sections were thereafter immunostained with antibodies to the myelin protein MBP, human nuclear antigen and stained with dapi to visualize nuclei, following the same procedures as described in Example 2.

Ex Vivo Transplantation
Ex vivo transplantation of the human ES-NSc on shiverer brain slices maintained as organotypic cultures, was effected according to the method described for murine ES-NSc (Zhang et al., 2006).

Electron Microscopy
Brain slices were fixed in 2.5% glutaraldehyde and 4% PFA in phosphate buffer (PB) 0.4 M, pH 7.4 for 12 hr, then cryoprotected in phosphate-buffered 30% sucrose overnight, and 20 µm-thick coronal sections were prepared from various regions. The sections were washed in 0.1 M Cacodylate buffer pH 7.4 and postfixed with 1% osmium tetroxide in the same buffer for 1-2 hours at RT. After en bloc staining with 2% uranylacetate in water for 1 hour at RT the slices were dehydrated in graded ethanol solutions and embedded in graded Epon 812, as previously described (Shinder and Devor 1994). Ultrathin sections (70-90 nm thickness) were prepared with Ultramicrotome Leica UCT, analyzed in a Philips Tecnai 12 Transmission Electron Microscope at 120 kV and digitized with Megaview III CCD camera using AnalySIS software.

Figures 4A, 4E:
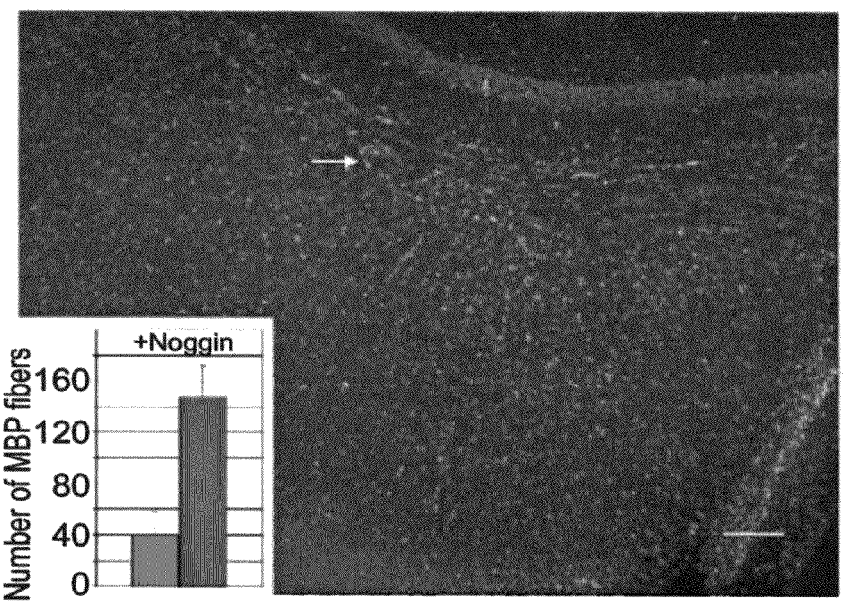
FIGS. 4 a-f depict the in vivo myelinating capacity of human ES cell derived neuroglial sphere cells (HuES-NSc) injected into brain of shiverer mice, which lack a functional gene for MBP. Any MBP staining seen is, therefore, the result of myelin synthesis by the exogenously transplanted cells. One month following HuES-NSc transplantation, brain sections were immunostained for MBP) and nuclei was visualized by dapi.
FIG. 4f shows nuclear dapi stain of the areas seen in FIGS. 4 c and 4 d, with ventricule (v), arrow and arrowhead depicting ventricle walls and migration into parenchyma, as in 4c. Star indicates the center of field in FIG. 4 d. Size bar 100 μm.
Figure 4B:
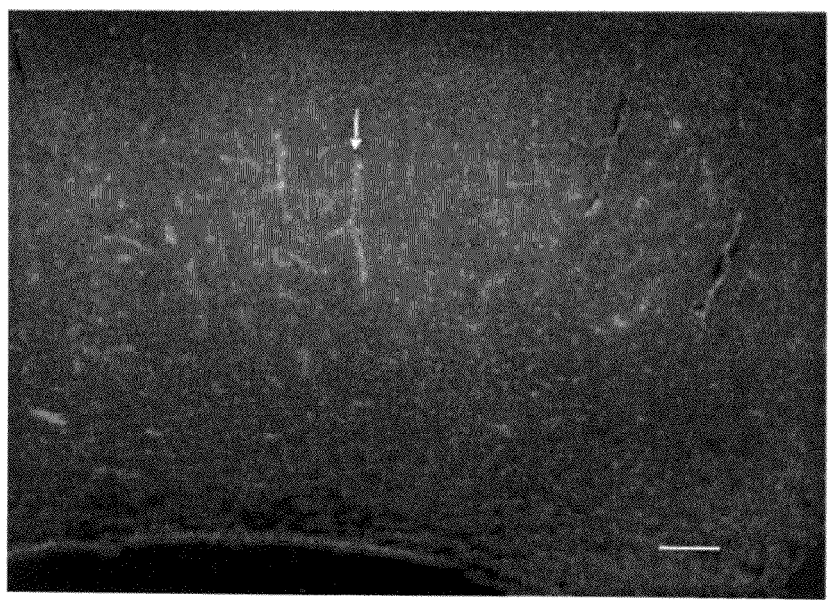
Figures 4C, 4D, 4F, 4G:
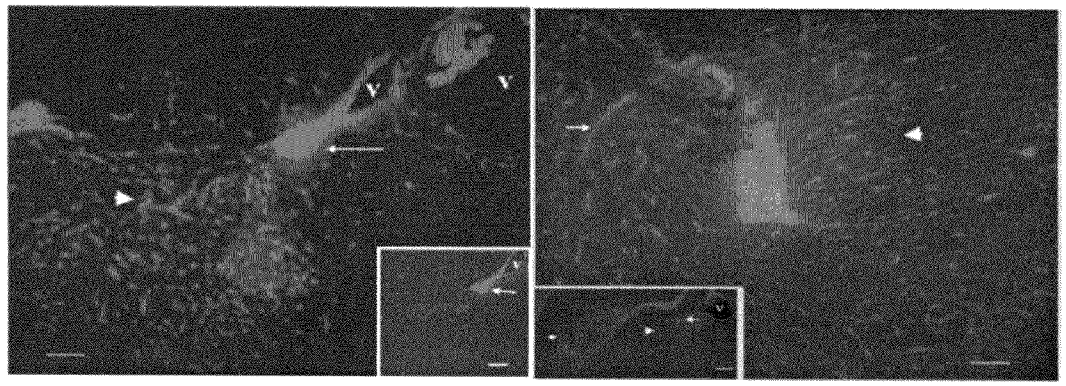

Results
The effect of noggin on HuES-NSc was examined in brain sections of Shiverer mice transplanted with HuES-NSc. Results show that cells treated with noggin (FIGS. 4 b-d) exhibit more MBP stained fibers than cells transplanted alone (FIG. 4 a). Quantitative analysis indicates that there is a significant 3.5-4 fold increase in the number of MBP fibers when noggin is added (FIG. 4 e). The fate of the injected human cells is illustrated FIGS. 4 c and f, which show MBP and nuclear dapi stain of the same brain area. The area includes part of the third ventricule (v) and MBP can be seen accumulating along the ventricule walls (arrow) and more importantly in the brain parenchyma (arrowhead) where fibers of various lengths are observed over a large area (FIG. 4 c). FIG. 4 g shows the same field stained for Human Nuclear Antigen (HNA) confirming the human origin of the myelinating cells. FIG. 4d shows an adjacent field (denoted by star in FIG. 4 f. These data demonstrate that the transplanted human cells produce myelin fibers over extended areas of the brain in the recipient animal.

Ex Vivo Transplantation of Human ES-NSc

Figures 5A, 5B:
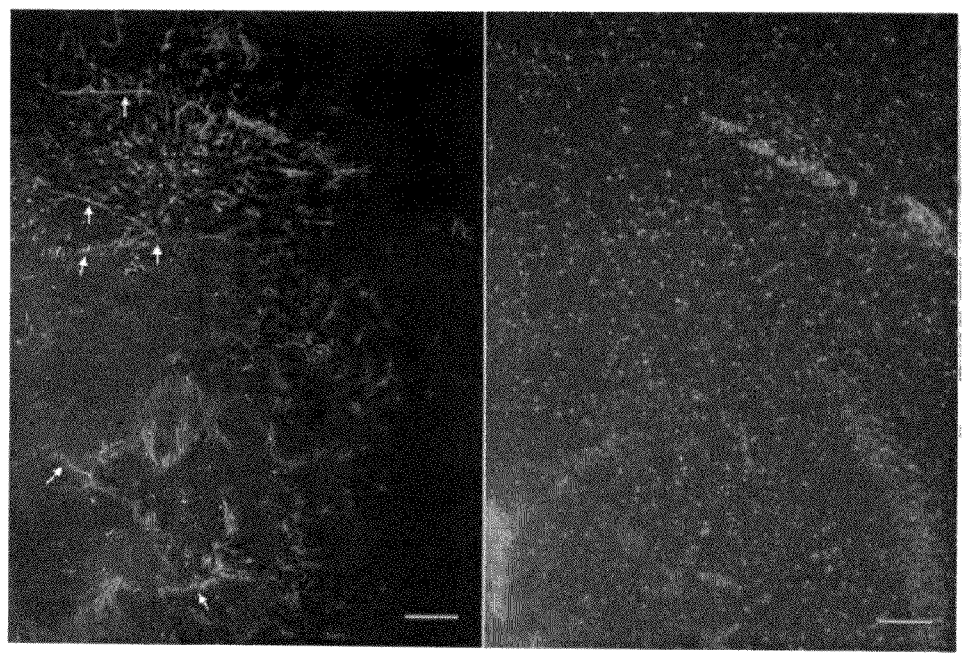
FIGS. 5 a-c,h are fluorescent light micrographs depicting the myelinating capacity of HuES-NSc in organotypic cultures of shiverer mouse (lacking a functional gene for MBP) brain slices.
Figure 5G:
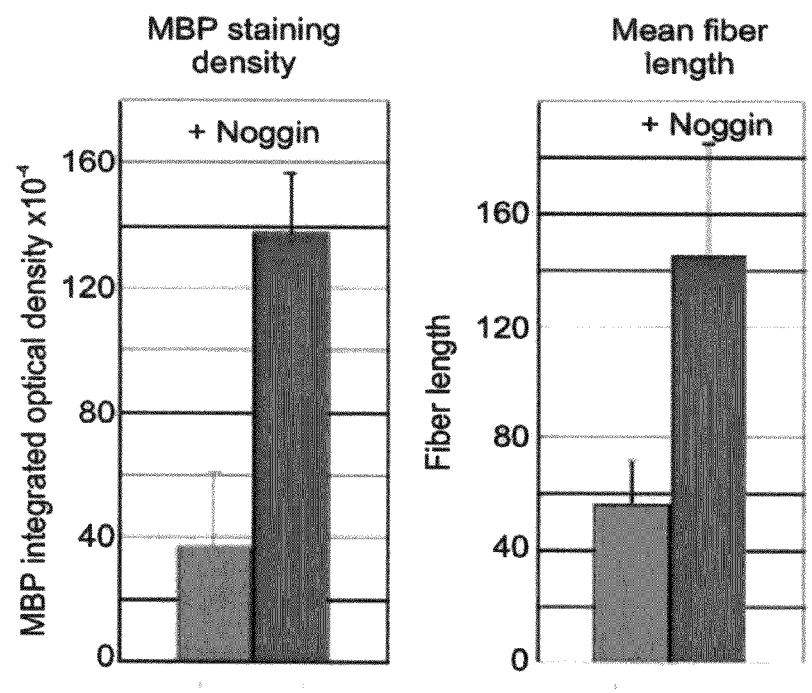

The myelinating capacity of the human ES-NSc was also demonstrated by ex-vivo transplantation on shiverer brain slices maintained as organotypic cultures. This method allows measuring the myelinating capacity of the implanted cells more rapidly than in vivo injections. Two weeks after implantation of HuES-NSc in the hippocampal region of a shiverer mouse brain slice, numerous MBP stained fibers were seen in an extended area of the entorhinal cortex (FIG. 5a; FIG. 5b shows the brain tissue nuclei with dapi-stain). At higher magnification, FIG. 5c shows formation of dense arrays of MBP-stained fibers, some of extended length (as indicated by arrows). Some of the fibers were a few hundred microns long (arrows), and dense arrays of similarly oriented and rather thick fibers were found (FIG. 5c). Few individual MBP$^+$ cells could be seen. Electron microscopy confirmed that compacted myelin sheaths, with major dense lines, were formed in the brain tissue transplanted with the noggin-treated huES-NS cells (FIG. 5e,f) contrasting with the dysmyelinated appearance of the shi/shi brain (FIG. 5d). Such figures of myelin were not seen with huES-NS cells untreated by noggin (which were like in FIG. 5d). The noggin treatment markedly enhanced the overall myelinating capacity, as quantitated by measuring the extent of MBP staining and the mean length of MBP$^+$ fibers formed (FIG. 5g).

Taken together, these results establish that the procedure described in the present invention yields human OP cells that can be expanded before engraftment and have the capacity to migrate and regenerate myelin fibers in brain of a dysmyelinated animal. The addition of noggin during the expansion stimulates the function of these OP cells to remyelinate.

Example 5

Derivation of Neurons from Human ES Cells

Materials and Experimental Procedures
Neuron Generating Culture

To attempt producing neurons from the human ES cells, a neuron-generating culturing procedure was devised, based on the culturing procedure described in Example 1, wherein step M (adherence to matrigel-coated plates) was omitted. Step R (treatment with retinoic acid) was done as in Example 1 but at the end of step S (neuroglial sphere ripening) the cells (dissociated by collagenase) were directly plated on poly-ornithine and fibronectin (PO—FN)-coated tissue culture plates (as described in Example 3. step D1) and cultured in ITTSSPP/B27 with EGF and bFGF (10 ng/ml each), alternating with EGF alone (20 ng/ml), for 10 days. Thereafter, the cells were passaged (1:2) by HBSS while scraped with a rubber policeman and the passage 2 cells were further cultured in the same conditions for an additional 6 days, after which the medium was changed to N2/B27 medium and the same growth factor regimen continued. For passage 3, the cells were dissociated with trypsin, plated 2 days with ITTSPP/B27, EGF 20 ng/ml, and then medium changed again to N2/B27, with EGF plus bFGF (10 ng/ml each) for 4 days. For passage 4, the cells were dissociated by trypsin, replated in N2/B27 with EGF plus bFGF for 2 days and then growth factors were removed, but laminin, vitamin C and noggin (50 ng/ml) were added (as in step F3 of Example 3). After 14 days the cells were fixed and stained. In an additional culturing procedure, 100 ng/ml Sonic Hedgehog (Shh; R&D Systems, Minneapolis, Minn.) was added in step R.

Results

Figure 6A:
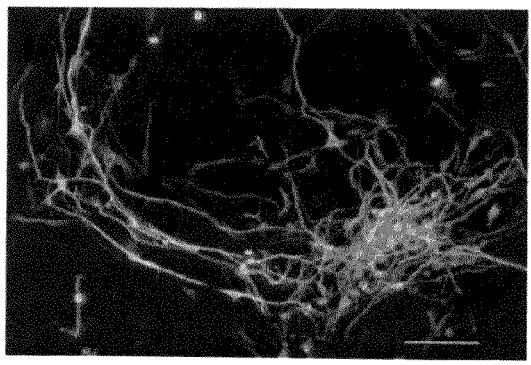
FIGS. 6 a-b depict neurons differentiated from Human ES cells which were stained for tubulin-βIII. Cells were cultured (as in Example 5) without (FIG. 6 a) or with (FIG. 6 b) Sonic Hedgehog (Shh) factor and with noggin. Size bar. 100 μm.

As indicated in Example 2, the huES-derived neurospheres (NS) cultured for 4 days on the adherent matrigel substrate (step M, as described in Example 1) formed a network of neurons, but these tended to disappear after prolonged culture on matrigel. To attempt producing neurons from the human ES cells, a neuron-generating culturing procedure was devised. The cultures contained neurons with long, connecting, processes (tubulin-βIII stain, FIG. 6a), indicating that these conditions are appropriate to develop neurons from the neurospheres. GFAP stain indicated that the cultures also contained astrocytes, but no oligodendrocytes developed from the O4 stained cells, which were round and appeared degenerating (not shown).

Figure 6B:
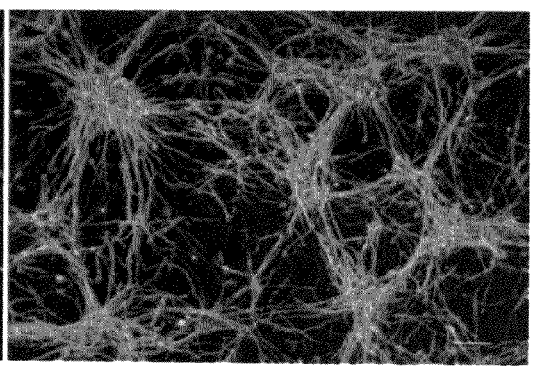

Sonic Hedgehog (Shh) is a factor made in the ventral spinal cord and plays an important role in inducing defined types of neurons as well as oligodendrocyte precursors (Marti and Bovolenta, 2002). When Shh was added in step R and the neuron-generating procedure described here was applied, there was an increase in the density of neuron network obtained (FIG. 6b). However, no oligodendrocyte developed even with Shh (not shown). Therefore, the described procedure can be useful to obtain populations of human neurons from huES cells, without the presence of oligodendrocytes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Other References are Cited Throughout the Document

Amit, M. and Itskovitz-Eldor, J., 2002. "Derivation and s pontaneous differentiation of human embryonic stem cells." J. Anat. 200, 225-232.

Amit, M., Shariki, C., Margulets, V. and Itskovitz-Eldor, J., 2004. "Feeder layer- and serum-free culture of human embryonic stem cells." Biol Reprod 70, 837-45.

Bain, G., Kitchens, D., Yao, M., Huettner, J. E. and Gottlieb, D. I., 1995. "Embryonic stem cells express neuronal properties in vitro." Dev Biol 168, 342-57.

Brustle, O., Jones, K. N., Learish, R. D., Karram, K., Choudhary, K., Wiestler, O. D., Duncan, I. D. and McKay, R. D., 1999. "Embryonic stem cell-derived glial precursors: a source of myelinating transplants." Science 285, 754-6.

Cao, Q., Benton, R. L. and Whittemore, S. R., 2002. "Stem cell repair of central nervous system injury." J Neurosci Res 68, 501-10.

Chandran, S, and Compston, A., 2005. "Neural stem cells as a potential source of oligodendrocytes for myelin repair." J Neurol Sci 233, 179-81.

Foster, L. M., Landry, C., Phan, T. and Campagnoni, A. T., 1995. "Conditionally immortalized oligodendrocyte cell lines migrate to different brain regions and elaborate 'myelin-like' membranes after transplantation into neonatal shiverer mouse brains." Dev Neurosci 17, 160-70.

Glaser, T., Perez-Bouza, A., Klein, K. and Brustle, O., 2005. "Generation of purified oligodendrocyte progenitors from embryonic stem cells." Faseb J 19, 112-4.

Gokhan, S., Marin-Husstege, M., Yung, S. Y., Fontanez, D., Casaccia-Bonnefil, P. and Mehler, M. F., 2005. "Combinatorial profiles of oligodendrocyte-selective classes of transcriptional regulators differentially modulate myelin basic protein gene expression." J Neurosci 25, 8311-21.

Goldman, S., 2005. "Stem and progenitor cell-based therapy of the human central nervous system." Nat Biotechnol 23, 862-71.

Grinspan, J., 2002. "Cells and signaling in oligodendrocyte development." J Neuropathol Exp Neurol 61, 297-306.

Gumpel, M., Baumann, N., Raoul, M. and Jacque, C., 1983. "Survival and differentiation of oligodendrocytes from neural tissue transplanted into new-born mouse brain." Neurosci Lett 37, 307-11.

Itsykson, P., Ilouz, N., Turetsky, T., Goldstein, R. S., Pera, M. F., Fishbein, I., Segal, M. and Reubinoff, B. E., 2005. "Derivation of neural precursors from human embryonic stem cells in the presence of noggin." Mol Cell Neurosci 30, 24-36.

Lachapelle, F., Gumpel, M., Baulac, M., Jacque, C., Duc, P. and Baumann, N., 1983. "Transplantation of CNS fragments into the brain of shiverer mutant mice: extensive myelination by implanted oligodendrocytes. I. Immunohistochemical studies." Dev Neurosci 6, 325-34.

Liu, S., Qu, Y., Stewart, T. J., Howard, M. J., Chakrabortty, S., Holekamp, T. F. and McDonald, J. W., 2000. "Embryonic stem cells differentiate into oligodendrocytes and myelinate in culture and after spinal cord transplantation." Proc Natl Acad Sci USA 97, 6126-31.

Marti, E. and Bovolenta, P., 2002. "Sonic hedgehog in CNS development: one signal, multiple outputs." Trends Neurosci 25, 89-96.

McDonald, J. W., Liu, X. Z., Qu, Y., Liu, S., Mickey, S. K., Turetsky, D., Gottlieb, D. I. and Choi, D. W., 1999. "Transplanted embryonic stem cells survive, differentiate and promote recovery in injured rat spinal cord." Nat Med 5, 1410-2.

McKay, R., 1997. "Stem cells in the central nervous system." Science 276, 66-71.

Mehler, M. F., Mabie, P. C., Zhang, D. and Kessler, J. A., 1997. "Bone morphogenetic proteins in the nervous system." Trends Neurosci 20, 309-17.

Mehler, M. F., Mabie, P. C., Zhu, G., Gokhan, S, and Kessler, J. A., 2000. "Developmental changes in progenitor cell responsiveness to bone morphogenetic proteins differentially modulate progressive CNS lineage fate." Dev Neurosci 22, 74-85.

Nistor, G. I., Totoiu, M. O., Haque, N., Carpenter, M. K. and Keirstead, H. S., 2005. "Human embryonic stem cells differentiate into oligodendrocytes in high purity and myelinate after spinal cord transplantation." Glia 49, 385-96.

Pfeiffer, S. E., Warrington, A. E. and Bansal, R., 1993. "The oligodendrocyte and its many cellular processes." Trends Cell Biol 3, 191-7.

Powers, J. M. and Rubio, A., 1995. "Selected leukodystrophies." Semin Pediatr Neurol 2, 200-10.

Reubinoff, B. E., Itsykson, P., Turetsky, T., Pera, M. F., Reinhartz, E., Itzik, A. and Ben-Hur, T., 2001. "Neural progenitors from human embryonic stem cells." Nat Biotechnol 19, 1134-40.

Roach, A., Takahashi, N., Pravtcheva, D., Ruddle, F. and Hood, L., 1985. "Chromosomal mapping of mouse myelin basic protein gene and structure and transcription of the partially deleted gene in shiverer mutant mice." Cell 42, 149-55.

Rogister, B., Ben-Hur, T. and Dubois-Dalcq, M., 1999. "From neural stem cells to myelinating oligodendrocytes." Mol Cell Neurosci 14, 287-300.

Schachner, M., Kim, S. K. and Zehnle, R., 1981. "Developmental expression in central and peripheral nervous system of oligodendrocyte cell surface antigens (O antigens) recognized by monoclonal antibodies." Dev Biol 83, 328-38.

Slutsky, S. G., Kamaraju, A. K., Levy, A. M., Chebath, J. and Revel, M., 2003. "Activation of myelin genes during transdifferentiation from melanoma to glial cell phenotype." J Biol Chem 278, 8960-8.

Thomson, J. A., Itskovitz-Eldor, J., Shapiro, S. S., Waknitz, M. A., Swiergiel, J. J., Marshall, V. S, and Jones, J. M., 1998. "Embryonic stem cell lines derived from human blastocysts." Science 282, 1145-7.

Warrington, A. E., Barbarese, E. and Pfeiffer, S. E., 1993. "Differential myelinogenic capacity of specific developmental stages of the oligodendrocyte lineage upon transplantation into hypomyelinating hosts." J Neurosci Res 34, 1-13.

Yandava, B. D., Billinghurst, L. L. and Snyder, E. Y., 1999. ""Global" cell replacement is feasible via neural stem cell transplantation: evidence from the dysmyelinated shiverer mouse brain." Proc Natl Acad Sci USA 96, 7029-34.

Zhang, P., Chebath, J., Lonai, P. and Revel, M., 2004. "Enhancement of oligodendrocyte differentiation from murine embryonic stem cells by an activator of gp130 signaling." Stem Cells 22, 344-54.

Zhang, P. L., Izrael, M., Ainbinder, E., Ben-Simchon, L., Chebath, J. and Revel, M., 2006. "Increased myelinating capacity of embryonic stem cell derived oligodendrocyte precursors after treatment by interleukin-6/soluble interleukin-6 receptor fusion protein." Mol Cell Neurosci 31, 387-98.

Zhang, S. C., Ge, B. and Duncan, I. D., 2000. "Tracing human oligodendroglial development in vitro." J Neurosci Res 59, 421-9.

Zhang, S. C., Wernig, M., Duncan, I. D., Brustle, O. and Thomson, J. A., 2001. "In vitro differentiation of transplantable neural precursors from human embryonic stem cells." Nat Biotechnol 19, 1129-33.

What is claimed is:

1. A method of enhancing myelination in the CNS of a subject, the method comprising directly administering at a site within the CNS of a subject in need thereof a therapeutically effective amount of an isolated oligodendrocyte or astrocyte, thereby enhancing myelination at the site of administration, wherein the isolated oligodendrocyte or astrocyte is generated by:
   (a) culturing in suspension human embryonic stem cells in the presence of retinoic acid and epidermal growth factor (EGF) to generate neurospheres;
   (b) contacting said neurospheres with EGF and bFGF on an adherent substrate, wherein said adherent substrate comprises an extracellular matrix component; and
   (c) contacting said neurospheres following step (b), wherein said neurospheres are intact or dissociated, with a medium comprising noggin, said medium being devoid of EGF and bFGF, thereby generating the oligodendrocyte or astrocyte.

2. The method of claim 1, wherein the subject suffers from a medical condition selected from the group consisting of autoimmune diseases, Guillan-Barre syndrome or congenital leukodystrophies, adrenoleukodystrophies, Pelizaeus-Merzbacher, Charcot-Marie-Tooth, Krabbe or Alexander disease, vanishing white matter syndrome, progressive multifocal leukoencephalopathy, infectious demyelinating diseases, postinflammatory demyelinated lesions, neurodegenerative diseases, multisystem degeneration, vascular diseases, ischemic white matter damage, vascular leukoencephalopathies, subcortical infarcts, brain trauma, spinal cord trauma, demyelinative injury, neoplasms and oligodendrio-glioma.

3. The method of claim 1, wherein said cells comprise oligodendrocytes and the subject suffers from insufficient myelination.

4. The method of claim 1, wherein said cells comprise astrocytes and the subject suffers from a medical condition selected from the group consisting of Alexander disease, epilepsy, Alzheimer's disease, spinal cord injury, traumatic brain injury and neurogenesis deficiencies.

* * * * *